(12) United States Patent
Teter et al.

(10) Patent No.: US 8,436,048 B1
(45) Date of Patent: May 7, 2013

(54) METHOD OF INHIBITING AB-TYPE BACTERIAL TOXINS AND TREATMENT FOR ASSOCIATED DISEASES

(75) Inventors: Kenneth Robert Teter, Oviedo, FL (US); Michael Prentice Taylor, Sanford, FL (US)

(73) Assignee: University of Central Florida Research Foundation, Inc., Orlando, FL (US)

( * ) Notice: Subject to any disclaimer, the term of this patent is extended or adjusted under 35 U.S.C. 154(b) by 697 days.

(21) Appl. No.: 12/537,543

(22) Filed: Aug. 7, 2009

Related U.S. Application Data

(60) Provisional application No. 61/086,918, filed on Aug. 7, 2008.

(51) Int. Cl.
*A61K 31/19* (2006.01)

(52) U.S. Cl.
USPC .......................................................... 514/570

(58) Field of Classification Search ................... 514/570
See application file for complete search history.

(56) References Cited

U.S. PATENT DOCUMENTS 5,708,025 A * 1/1998 Samid ........................... 514/538

OTHER PUBLICATIONS

Esuvaranathan et al. "A study of 245 infected surgical wounds in Singapore." The Journal of Hospital Infectrion, 1992, vol. 21, No. 3, pp. 231-240.*
Daniels "Concerning the physical properties of solutions of certain phenyl-substituted acids in relation to their bactericidal power," Journal of Physical Chemistry, 1931, vol. 35, pp. 2049-2060.*

* cited by examiner

*Primary Examiner* — Shengjun Wang
(74) *Attorney, Agent, or Firm* — Timothy H. Van Dyke; Beusse, Wolter, Sanks, Mora & Maire, P.A.

(57) ABSTRACT

Disclosed herein are compounds useful in inhibiting the action of AB-type bacterial toxins such as cholera, traveler's diarrhea, enterohemorrhagic diarrhea caused by *E. coli* O157:H7 and pertussis or whooping cough. Also included in the invention is the use of these compounds in treatment of diseases associated with those toxins.

17 Claims, 26 Drawing Sheets ic intoxication. The
METHOD OF INHIBITING AB-TYPE BACTERIAL TOXINS AND TREATMENT FOR ASSOCIATED DISEASES

RELATED APPLICATION

This application claims priority from provisional application Ser. No. 61/086,918, which was filed on 7 Aug. 2008 and which is incorporated herein by reference in its entirety.

STATEMENT OF GOVERNMENT RIGHTS

The invention claimed herein was made with at least partial support from the U.S. Government through NIH grants R01 AI073783, K22 AI054568 and R03 AI067987 to K. Teter. Accordingly, the government may have certain rights in the invention, as specified by law.

FIELD OF THE INVENTION

This invention relates to infectious diseases and, more specifically, to inhibitors of bacterial toxins of the type having a catalytic A subunit and a cell-binding B subunit and, especially to those within this group which function as ADP-ribosylating toxins.

BACKGROUND OF THE INVENTION

Bacterial toxins have been known to be primary mediators of a number of diseases both of the intestinal tract and of other organ systems. Some bacterial toxins are known as AB-type toxins, since they are composed of a catalytic A subunit and a cell-binding B subunit. Examples of such AB-type toxins include cholera toxin (CT), the *E. coli* heat-labile toxin (LT) responsible for traveler's diarrhea, the *B. pertussis* toxin responsible for much of the symptomatology of whooping cough, exotoxin-A produced by *Pseudomonas aeruginosa* strains often found in the respiratory tract of cystic fibrosis patients or on the damaged skin of burn patients, Shiga toxin produced in the intestinal disease shigellosis, and the similar toxin produced by enterohemorrhagic *E. coil* and which has lately been associated in the U.S. with contaminated produce and ground beef products.

Typically, the diseases caused by these bacterial toxins are treated symptomatically because drugs effective against the toxins themselves have not been available. Except in the case of pertussis, prior immunizations have either not been available or have not been very successful in conferring a protective immunity against these toxins.

Accordingly, there is a great need for drugs that would act directly against these toxins, interfering with their mechanisms of action so as to prevent entry of the active toxin into targeted host cells and cellular intoxication. The present invention provides such long-needed drugs and discloses a proposed new model mechanism by which extracellular AB-type toxins gain access to the affected cells of the body.

SUMMARY OF THE INVENTION

With the foregoing in mind, the present invention advantageously provides a new understanding of the mechanisms of action of AB-type bacterial toxins at the cellular level and identifies compounds which are able to block these toxins' biologic activity, consequently, the compounds are useful in methods of treatment of the respective diseases.

Our soon to be published paper titled "Stabilization of the Tertiary Structure of the Cholera Toxin A1 Subunit Inhibits Toxin Dislocation and Cellular Intoxication" provides proof-of-principle for an anti-toxin therapeutic strategy that blocks the thermal unfolding of the toxin A chain. This paper was filed as part of the provisional application to which priority is claimed herein. As demonstrated in this experimental work, which is further expanded below, the inhibition of A chain unfolding prevents toxin passage into the cytosol and, hence, prevents productive intoxication.

Also further detailed below are data from our study entitled "Hsp90 is Required for Transfer of the Cholera Toxin A1 Subunit from the Endoplasmic Reticulum to the Cytosol." These data demonstrate that geldanamycin (GA), an inhibitor of heat shock protein 90 (Hsp90), blocks toxin passage into the cytosol, also blocking productive intoxication. This experimental work shows that (i) Hsp90 binds directly to the catalytic CTA1 subunit with high affinity; (ii) GA blocks the binding of Hsp90 to CTA1; (iii) GA blocks CTA1 passage from the endoplasmic reticulum (ER) to the cytosol; and (iv) GA blocks CT intoxication in cultured cells and in the physiological ileal loop model of toxin-induced diarrhea. We have found that GA is effective in blocking CT intoxication in cultured cells at a level of 0.1 µM.

We have also now shown that sodium 4-phenylbutyrate (PBA) blocks CT activity against cultured cells in a dose-dependent manner. Additionally, we have shown that PBA blocks CTA1 export to the cytosol. One of our collaborating laboratories has reported that PBA also blocks CT activity in the ileal loop test system. As with ricin and exotoxin A, neither GA nor PBA have, so far, shown to inhibit Shiga toxin activity against cultured cells.

Yet additionally, we have generated preliminary evidence that both GA and PBA will be effective against pertussis toxin (PT). We have shown that Hsp90 binds to the catalytic subunit of PT (PTS1) in an ATP-dependent manner that is inhibited by GA. We have also shown that PBA inhibits the thermal unfolding of PTS1. Intoxication assays with PT and GA or PBA remain to be completed.

PBA is an FDA approved drug. The maximal FDA approved dose of PBA for therapeutic use is 20 g/d, which produces PBA serum levels between 600 and 1,700 uM. This is from oral administration of four 500 mg tablets over the course of a day. We have shown that PBA is effective against CT intoxication of cultured cells at a concentration ranging from 10-100 µM. This concentration is well below the maximum permissible serum level of PBA. In addition, as noted above, a dose of 20 g/d produces serum levels of PBA between 600 and 1,700 uM, however, it is not necessary to deliver PBA to the serum, but only that it be present in the intestines, which is where it would be delivered by oral administration. Thus, an effective dose of PBA is deliverable to the intestinal epithelium with a drug concentration far below the maximal dosage. Two published papers that have reported PBA as a therapeutic "chemical chaperone" for treating genetic diseases are by A. F. Collins et al., "Oral sodium phynylbutyrate therapy in homozygous beta thalassemia: a clinical trial"; *Blood*, 1995, 85:43-49; and Jeffrey H. Teckman, "Lack of effect of oral 4-phenylbutyrate on seum alpha-1-antitrypsin in patients with α-1-antitrypsin deficiency: a preliminary study"; *J. Ped. Gastroenterology and Nutrition*, July 2004, 39:34-37. These two papers report PBA serum levels between 600 and 1,700 uM.

BRIEF DESCRIPTION OF THE DRAWINGS

Some of the features, advantages, and benefits of the present invention having been stated, others will become apparent as the description proceeds when taken in conjunction with the accompanying drawings, presented for solely for exemplary purposes and not with intent to limit the invention thereto, and in which.

DETAILED DESCRIPTION OF THE PREFERRED EMBODIMENT

Figure 1:
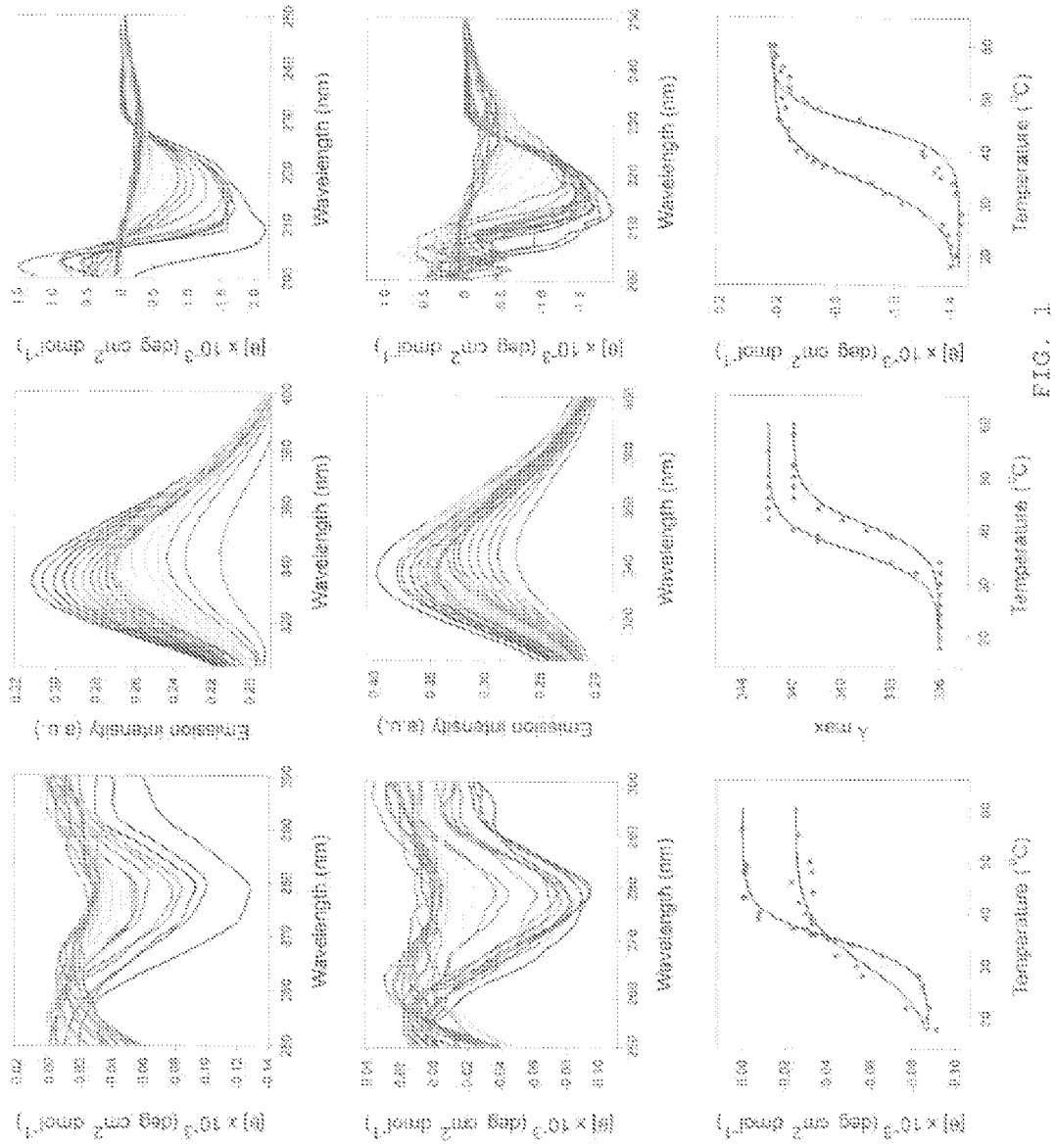
FIG. 1 shows stability curves for the catalytic CTA1 subunit in the absence or presence of sodium 4-phenylbutyrate (PBA), as demonstrated by near-UV circular dichroism (CD), fluorescence spectroscopy, and far-UV CD (from left to right, respectively, in the figure)
Figure 2:
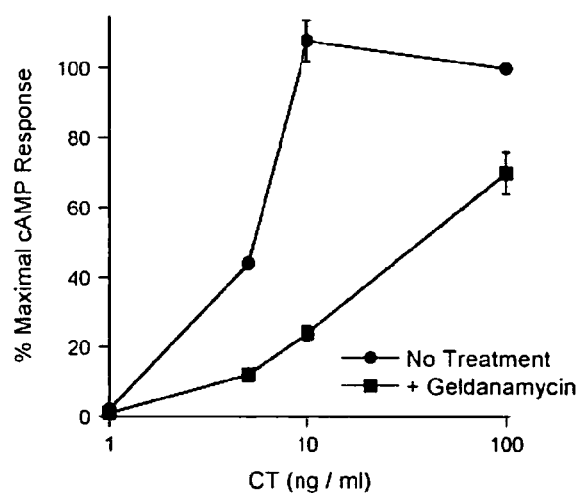
FIG. 2 demonstrates lowered CT toxicity to cells in culture when the cells are treated with geldanamycin (GA)
Figure 3:
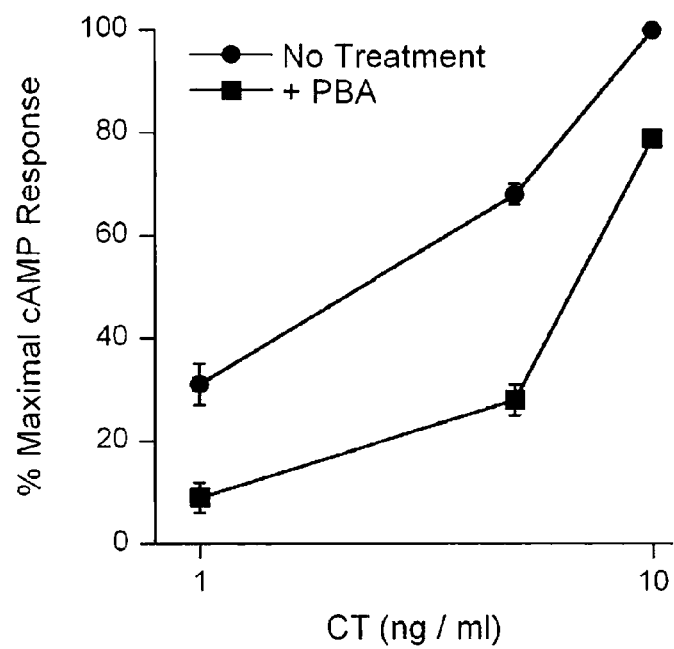
FIG. 3 is a line graph showing the effect of PBA treatment on the cellular toxicity of up to 10 ng/ml CT.

The present invention will now be described more fully hereinafter with reference to the accompanying drawings, in which preferred embodiments of the invention are shown. Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. Any publications, patent applications, patents, and other references mentioned in this application are incorporated herein by reference in their entirety. In case of conflict, the present specification, including any definitions, will control. In addition, it should be understood that the materials, methods and examples given are illustrative in nature only and not intended to be limiting. Accordingly, this invention may be embodied in many different forms and should not be construed as limited to the illustrated embodiments set forth herein. Rather, these illustrated embodiments are provided so that this disclosure will be thorough and complete, and will fully convey the scope of the invention to those skilled in the art. Other features and advantages of the invention will be apparent from the following detailed description, and from the claims.

Our paper published in *Journal of Molecular Biology*, (2007) 374, 1114-1128 presents the first experimental data demonstrating that isolated cholera toxin A1 polypeptide (CTA1) is a thermally unstable protein. CTA1 is held in a stable conformation by its association with CTA2/CTB5, but it can spontaneously unfold at physiological temperature when separated from the holotoxin in the endoplasmic reticulum (ER). We have proposed a new model of CTA1 translocation from the ER in that this spontaneous unfolding event triggers the endoplasmic reticulum-associated degradation (ERAD) system to mediate CTA1 export to the cytosol. In contrast, the currently accepted model of CTA1 translocation treats CTA1 as a stable protein that requires chaperone-mediated unfolding in the ER. The current model also propounds that CTA1 stability provides the driving force for extraction from the ER, that is, the old model holds that as unfolded CTA1 emerges from the Derlin-1 channel, it spontaneously refolds in the cytosol and thereby gains directionality for its movement across the ER membrane because the refolding would prevent it from sliding back into the channel. However, in our newly proposed model, because CTA1 is actually in an unfolded conformation at 37° C., we hypothesize that a cytosolic chaperone must provide the driving force for CTA1 export from the ER. Accordingly, under our new model, stabilization of the heat-labile CTA1 polypeptide within the ER could prevent its ERAD-mediated export to the cytosol and, consequently, could also prevent CT intoxication. Furthermore, based on our new model, CT passage into the cytosol and cellular intoxication could also be prevented by inhibition of the cytosolic chaperone that provides the driving force for CTA1 export from the ER.

Additionally, our soon to be published paper titled "Stabilization of the Tertiary Structure for the Cholera Toxin A1 Polypeptide Inhibits Toxin Dislocation and Cellular Intoxication" presents proof-of-principle for the concept of our new model. We used glycerol, a known "chemical chaperone" that stabilizes protein structures, to inhibit the thermal unfolding of CTA1. Glycerol also prevented CTA1 export to the cytosol (results not shown) and CT intoxication. However, glycerol is not a viable therapeutic option since it would be toxic to the patient. We therefore undertook a search for non-toxic potentially effective drugs (see also, Perlmutter, D. H., Chemical Chaperones: A Pharmacological Strategy for Disorders of Protein Folding and Trafficking, *Pediatric Research,* 52(6), 832-836).

Our search identified sodium 4-phenylbutyrate (PBA) as a potential non-toxic drug candidate. PBA, like glycerol, is another chemical chaperone but it is tolerated by humans and is actually an FDA-approved drug for treating diseases related to urea cycle enzyme deficiencies. Our experimental work disclosed in the priority provisional application (document titled "A Therapeutic Chemical Chaperone Inhibits Cholera Intoxication and Unfolding/Translocation of the Cholera Toxin A1 Subunit") showed that PBA prevents the thermal unfolding of CTA1 and also prevents CT intoxication of cultured cells. Experiments now underway, we predict will show that PBA prevents CTA1 export from the ER into the cytosol.

Since we hypothesize that this drug may have real therapeutic potential for treating CT, and possibly other toxin-mediated diseases, we are further investigating if it also demonstrates a CTA1 inhibitory effect in a physiological model of intoxication—the ileal loop system. If, as expected, PBA blocks intoxication in ileal loops, this would provide strong support for our new proposed mechanism of action of CTA1 and how this toxin may be counteracted.

A second anti-toxin therapeutic agent we have identified is geldanamycin (GA), an inhibitor of hsp90. GA has received a attention as a potential anti-cancer agent (see the review article by Blagosklonny, M. V., Hsp-90-associated oncoproteins: multiple targets of geldanamycin and its analogs, *Leukemia* (2002) 16, 456,462). GA itself was initially found to be too toxic for therapeutic use, but second generation GA derivatives have proven effective in phase I clinical trials. We theorized that because hsp90 is required for the endosome-to-cytosol translocation of diphtheria toxin and the clostridial ADP-ribosylating toxins, GA might provide a good target for a therapeutic drug. See the following: Ratts et al., The cytosolic entry of diphtheria toxin catalytic domain requires a host cell cytosolic translocation factor complex, *J. Cell Biol.*, 160 (7), 1139-1150 (2003); Haug et al., The Host Cell Chaperone Hsp90 Is Essential for Translocation of the Binary *Clostridium botulinum* C2 Toxin into the Cytosol, *J. Biological Chem.*, 278(34), 32266-32274 (2003); Haug et al., The Host Cell Chaperone Hsp90 Is Necessary for Cytotoxic Action of the Binary Iota-Like Toxins, *Infection and Immunity*, 72(5), 3066-3068 (2004); and Marissa V Powers and Paul Workman, Targeting of multiple signaling pathways by heat shock protein 90 molecular chaperone inhibitors, *Endocrine-Related Cancer* (2006) 13 S125-S135.

Moreover, we have now shown by surface plasmon resonance (SPR) that hsp90 interacts directly with CTA1 and that this interaction is inhibited by GA. CT intoxication is also blocked in GA-treated cells (attached). We are further improving the translocation assay to determine if GA prevents the ER-to-cytosol export of CTA1. We theorize that Hsp90 is the cytosolic chaperone that provides the driving force for extraction of CTA1 and other ADP-ribosylating toxins from the ER.

The data shown graphically in FIG. 1 also help to explain Table 1. The data in FIG. 1 are raw measurements from three biophysical techniques, near-UV circular dichroism (CD), fluorescence spectroscopy, and far-UV CD (from left to right, respectively, in the figure). Near-UV CD and fluorescence spectroscopy provide two different measures of protein tertiary structure. Far-UV CD provides a measurement of secondary structure. Certain linear arrangements of amino acids will spontaneously assume common shapes known as α-helices and β-sheets. These shapes are the secondary structure of a protein. The linear order of amino acids is the primary structure. The overall three dimensional structure of a protein which is ordered around the secondary structures is the protein tertiary structure. In the tertiary structure of a properly folded protein, the hydrophobic amino acids should be buried within the protein and protected from the aqueous environment. The measurements of tertiary structure detect the solvent exposure of the hydrophobic amino acids; this is indicative of protein unfolding. Each line in the raw data shown in FIG. 1 (top 6 panels) represents a measurement at a different temperature, with the color shift from blue to red corresponding to a shift in temperature from 18 to 65° C. The top row presents measurements taken for the catalytic A1 polypeptide of cholera toxin (CTA1), and the middle row are measurements taken for CTA1 in the presence of 100 μM PBA. The bottom row is an analysis of the top two rows in which protein unfolding is plotted as a function of temperature. Low Y axis values represent folded conformations of the toxin, while high Y axis measurements represent unfolded conformations of the toxin. The high values plateau when the final unfolded state is reached. From these sigmoidal curves, we can calculate how much initial protein structure remains at each temperature. The point at which 50% of the initial structure is lost is called the transition temperature ($T_m$). It is the Tm values that are listed in the Table. The Figure of the raw data and unfolding curves only shows the data for 100 μM PBA, but we also ran experiments for 1 and 10 μM PBA. The processed data for these experiments are in the Table, which shows there is some stabilization of all

TABLE 1

| Concn (PBA in μM) | Melting temperature ($T_m$) | | |
|---|---|---|---|
| | Near UV (° C.) | Far UV (° C.) | Fluorescence (° C.) |
| 1 | 33.0 | 37.0 | 37.5 |
| 10 | 35.0 | 39.0 | 38.5 |
| 100 | 35.0 | 44.0 | 41.0 |
| ∅ | 30.0 | 35.0 | 36.0 |

∅—in the absence of PBA three CTA1 structural parameters even at 1 μM PBA. Higher PBA concentrations provide a higher level of structural stabilization, meaning higher temperatures are required to unfold CTA1. Interestingly, even in the presence of PBA the $T_m$ values are still near physiological temperature. Given that even 1 μM PBA has some inhibitory effect on CT intoxication, this must mean that substantial unfolding of CTA1 is required to trigger its export to the cytosol where its target resides.

The graphs shown in FIG. 1 plot the cellular effect of CT intoxication. CT-treated cells generate elevated levels of cAMP which we measure. The maximal cAMP response for all conditions is set at 100%, and all other cAMP values are expressed as a percentage of this maximal value. Cells are treated with toxin for 2 continual hours before measurement, and PBA is added simultaneously with the toxin. The first graph is the result with 1 μM PBA, and the second graph is the result with 100 μM PBA. The control curves (results without PBA) differ from the two graphs because two different assay kits for used for the experiments, and the second kit (with 100 μM PBA) has a better detection range. We are now standardizing all of our experiments by just using the second kit. Fold-resistance is determined from the half-maximal effective concentrations (toxin concentration that gives an effect 50% of the maximum). For 1 μM PBA, we see a 3.5-fold level of toxin resistance. We can't calculate fold resistance for 100 μM PBA because in the presence of PBA we didn't reach a 50% value even at the highest toxin concentration. So 100 μM PBA works pretty well, at least in cell culture.

We have also conducted additional experiments to determine the binding affinity of PBA for CTA1. Although not shown here, the data indicate that PBA binds to CTA1 and the CT holotoxin (which would include CTA1), but it does not bind to the cell-binding B subunit of CT. Accordingly, there is some specificity to the toxin-PBA interaction, which is unexpectedly surprising. PBA appears to bind to CTA1/CT with ~100 μM affinity, which represents a very high affinity interaction (tight binding).

Accordingly, this disclosure teaches that at least these two therapeutics, PBA and GA, are effective in suppressing entry of an AB-type bacterial toxin, particularly an ADP-ribosylating toxin such as CTA1 into the host cell cytosol and also mitigates or prevents toxicity to the cells themselves. Additionally, given the high degree of similarity between CT and *E. coli* LT we believe that in a prophetic example we can predict that PBA and GA may also be effective in blocking LT intoxication. Moreover, we also theorize it will be fruitful to test a combination of both PBA and GA. Since PBA and GA block separate steps in the translocation process, they may have an additive effect on toxin inhibition.

The toxins/diseases which we initially expected might be inhibited by GA and/or PBA included the following:
1. cholera toxin/cholera;
2. E. coli heat-labile toxin/traveler's diarrhea;
3. pertussis toxin/whooping cough;
4. exotoxin A/infections with Pseudomonas aeruginosa (particularly in cystic fibrosis patients or in burn victims); and
5. Shiga toxin/shigellosis and food-borne outbreaks of enterohemorrhagic E. coli (O157:H7).

The order shown for the toxins listed is the expected order of likelihood for drug-induced toxin resistance. GA inhibits Hsp90 function, and Hsp90 may specifically recognize and interact with ADP-ribosylating toxins. CT and LT are very similar ADP-ribosylating toxins, so that PBA and GA should work against both of them. Pertussis toxin is an ADP-ribosylating toxin and is very unstable, so there is a reasonable basis for expecting that both PBA and GA will work against this toxin.

Our experiments with exotoxin A (ETA) only showed weak drug-induced resistance, although we still need to test the PBA/GA combination treatment. ETA is also an ADP-ribosylating toxin, so we expected GA to work against it. The stability of ETA is unknown, but our new model predicts all AB-type (catalytic A subunit, cell-binding B subunit) ER-translocating toxins will have an unstable A chain.

Shiga toxin is not an ADP-ribosylating toxin, thus, we expected a lower probability that GA would be effective against it. The stability of Shiga toxin is unknown, but we predict it is unstable and that it will, therefore, be affected/inhibited by PBA.

PBA and GA did not inhibit ricin. Ricin is not an ADP-ribosylating toxin, so we did not expect GA to have an effect. The unfolding of ricin A chain in the ER is facilitated by an interaction with the lipids of the inner leaflet of the ER membrane, so it may be that PBA cannot inhibit the assisted unfolding of a toxin A chain.

Reviewing recent articles on chemical chaperones for potential drug candidates it appears that besides PBA, other chemical chaperones potentially useful in this invention include glycerol, deuterated water, DMSO, and trimethylamine N-oxide (TMAO). These other reagents work in cell culture but, due to toxicity, not so well in patients. In general, there has been a shift to more specific "pharmacological chaperones" which are designed to only function against the targeted protein. PBA and the chemical chaperones are less specific than pharmacological chaperones and can affect many proteins. We expected that there would be non-toxic chemical chaperones other than PBA, but after a literature search it seems that PBA may be the only therapeutic chemical chaperone presently available.

A Therapeutic Strategy: Blocking Unfolding of Toxin A Chain Summary

Cholera toxin (CT) moves from the cell surface to the endoplasmic reticulum (ER) by retrograde vesicular transport. The catalytic subunit of CT (CTA1) then crosses the ER membrane and enters the cytosol in a process that involves the quality control mechanism of ER-associated degradation (ERAD). The molecular details of this dislocation event are poorly characterized. Here, we report that thermal instability in the CTA1 subunit—specifically, the loss of CTA1 tertiary structure at 37° C.—triggers toxin dislocation. Biophysical studies found that glycerol preferentially stabilized the tertiary structure of CTA1 without having any noticeable effect on the thermal stability of its secondary structure. The thermal disordering of CTA1 tertiary structure normally preceded the perturbation of its secondary structure, but in the presence of 10% glycerol the temperature-induced loss of CTA1 tertiary structure occurred at higher temperatures in tandem with the loss of CTA1 secondary structure. The glycerol-induced stabilization of CTA1 tertiary structure blocked CTA1 dislocation from the ER and instead promoted CTA1 secretion into the extracellular medium. This, in turn, inhibited CT intoxication. Glycerol treatment also inhibited the in vitro degradation of CTA1 by the core 20S proteasome. Collectively, these findings indicate that toxin thermal instability plays a key role in the intoxication process and that an agent that increases the stabilization of CTA1 tertiary structure is a potential anti-toxin therapeutic drug.

Introduction

Cholera toxin (CT) is an $AB_5$ protein toxin that ADP-ribosylates and activates the stimulatory a subunit of the heterotrimeric G protein ($G_{s\alpha}$).[1,2] The catalytic A moiety of CT is synthesized as a CTA protein of 27 kDa molecular mass. Nicking of CTA by the Vibrio cholerae hemagglutinin protease or other proteases generates a disulfide-linked CTA1/CTA2 heterodimer. Enzymatic activity is a property of the 22 kDa CTA1 subunit, while the 5 kDa CTA2 subunit interacts non-covalently with the B pentamer and thereby tethers CTA1 to the CTB domain. The cell-binding B moiety of CT is assembled from 12 kDa monomers as a homopentameric ring-like structure that adheres to GM1 gangliosides on the eukaryotic plasma membrane.

A substantial portion of surface-bound CT is delivered to the lysosomes and degraded, but the functional pool of toxin is instead transported to the endoplasmic reticulum (ER) through a series of vesicular trafficking events.[3-6] The resident redox state of the ER reduces the CTA1/CTA2 disulfide bond, which then permits chaperone-assisted dissociation of CTA1 from $CTA2/CTB_5$.[7-9] The isolated CTA1 subunit subsequently crosses the ER membrane and enters the cytosol where it interacts with $G_{s\alpha}$. Activated $G_{s\alpha}$ stimulates adenylate cyclase function and the production of cAMP. This leads to the opening of chloride channels on the apical face of intoxicated intestinal epithelial cells; the osmotic movement of water which follows chloride efflux into the gut generates the profuse watery diarrhea of cholera.[1,2]

To move from the ER to the cytosol, CTA1 uses the ER-associated degradation (ERAD) dislocation mechanism.[9-13] ERAD recognizes misfolded or misassembled proteins in the ER and exports them to the cytosol for degradation by the 26S proteasome.[14] CTA1 export probably occurs through Sec61 and/or Derlin-1 protein-conducting channels in the ER membrane.[15-17] Although CTA1 is processed as an ERAD substrate, it avoids the standard ERAD route of ubiquitin-dependent proteasomal degradation because its arginine-over-lysine bias limits the number of potential sites for ubiquitin conjugation.[18] Other AB toxins such as Shiga toxin and ricin also move from the cell surface to the ER and exploit ERAD for entry into the cytosol.[19,20]

Two major predictions have been derived from the ERAD model of CTA1 dislocation: (i) the C-terminal hydrophobic region of CTA1 (residues 162-192; the $A1_3$ subdomain) triggers ERAD-mediated toxin entry into the cytosol; and (ii) the translocated pool of CTA1 is stable in the eukaryotic cytosol.[6,21] It is hypothesized that components of the ERAD machinery interact with the $CTA1_3$ subdomain and subsequently unfold the toxin for passage into the cytosol.[9] CTA1 is then thought to spontaneously refold in the cytosol, producing a stable conformation that is resistant to proteasomal degradation.[18]

We have shown that the CTA1$_3$ subdomain is not required for toxin entry into the cytosol and that the translocated pool of CTA1 is not stable in the cytosol.[10,22] Both observations may be linked to the unstable, heat-labile nature of the CTA1 subunit.[23,24] CTA1 is held in a stable conformation when associated with other components of the holotoxin,[24-26] but it can unfold spontaneously after dissociation from CTA2/CTB$_5$.[24] This unfolding event would activate the ERAD system and thereby promote CTA1 export to the cytosol. Following dislocation into the cytosol, CTA1 could retain significant enzymatic activity because of its association with host proteins such as the ADP-ribosylation factors that serve as co-factors to enhance CTA1 activity.[23,24,27] However, the structural state of the isolated CTA1 subunit leaves it susceptible to ubiquitin-independent degradation by the core 20S proteasome.[24] With this model of toxin-ERAD interactions, an inherent physical property of the CTA1 subunit (i.e., thermal instability) is linked to both toxin dislocation into the cytosol and toxin degradation in the cytosol. Our model suggests CTA1 is processed as a typical misfolded/unfolded ERAD substrate, whereas a prevailing model of toxin dislocation treats CTA1 as a stable protein that requires chaperone-assisted unfolding in order to move from the ER to the cytosol.[6,9,16,18,28]

According to our model, structural stabilization of the CTA1 subunit will inhibit CTA1 dislocation and thereby prevent CT intoxication. The thermal stabilization of CTA1 should also block its degradation by the 20S proteasome, which only acts upon unfolded substrates.[29] To test these predictions, we examined the impact of glycerol on CTA1 structure, CTA1 dislocation/degradation, and CT intoxication. Glycerol is a chemical chaperone that stabilizes protein structures and is commonly used to disrupt ERAD-substrate interactions.[30-34] Glycerol has also been shown, by an unknown mechanism, to protect cultured cells against intoxication with either ricin or Shiga toxin 2.[35,36] In this work we show that glycerol prevents the temperature-induced loss of CTA1 tertiary structure, which in turn prevents CTA1 dislocation into the cytosol and productive intoxication. Glycerol also inhibited the in vitro degradation of CTA1 by the 20S proteasome. These observations provide mechanistic insight into the molecular events underlying CTA1-ERAD interactions and suggest a new therapeutic approach for anti-toxin countermeasures.

Results

Effect of Glycerol on CTA1 Protease Sensitivity

Figure 7:
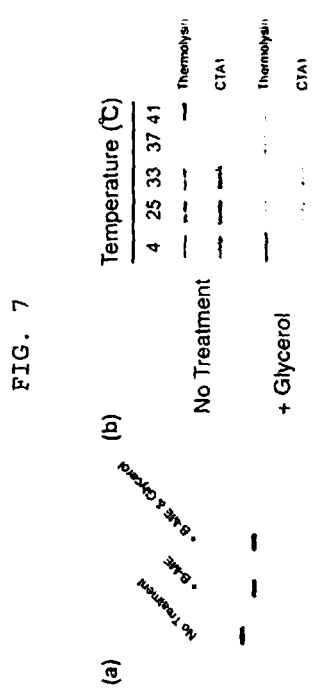

As a first step toward evaluating the stabilizing effect of glycerol on CTA1 structure, we employed a protease sensitivity assay (FIG. 7). A final concentration of 10% glycerol was used in order to maintain consistency with other reports that have used this concentration of glycerol to disrupt ERAD-substrate and/or host-toxin interactions.[31-33,35,36] Protease sensitivity assays are used to probe the folding state of a protein, as proteins often become more susceptible to proteolysis upon (partial) unfolding.[9,24,37] Samples of the reduced CTA1/CTA2 heterodimer were incubated in the absence or presence of 10% glycerol for 45 minutes at 4° C., 25° C., 33° C., 37° C., or 41° C. All samples were then placed on ice and exposed to thermolysin, a metalloendoprotease that cleaves the peptide bonds in proteins at the surface-exposed hydrophobic residues. EDTA and sample buffer were added after 45 minutes to halt the digests, and the samples were subsequently resolved by sodium dodecyl sulfate polyacrylamide gel electrophoresis (SDS-PAGE) with Coomassie staining. Since all protease treatments were performed at 4° C., differential degradation of the toxin samples could only result from temperature-induced changes to the structure of CTA1.

Previous work has shown that our reducing condition of 10 mM β-mercaptoethanol (β-ME) is sufficient for complete separation of CTA1 from CTA2;[24] this result was also confirmed for CTA1/CTA2 heterodimers incubated with 10 mM β-ME and 10% glycerol (FIG. 7(a)). Reduction of the CTA1/CTA2 disulfide bond is necessary to examine the temperature dependence of CTA1 protease sensitivity because the covalent association of CTA1 with CTA2 provides a degree of conformational stability to CTA1 which prevents its proteolysis by thermolysin.[24]

The isolated CTA1 subunit was largely resistant to thermolysin-mediated proteolysis when incubated at temperatures up to 33° C., but CTA1 shifted to a protease-sensitive state at 37° C. This was evidenced by a substantial weakening of the CTA1 band in the gel when the toxin was preincubated at temperatures above 33° C. before thermolysin treatment (FIG. 7(b)). Little change in CTA1 band intensities were observed in the temperature range of 4° C. to 41° C. for toxin samples treated with 10% glycerol, indicating that treatment with 10% glycerol prevented the transition of CTA1 to a protease-sensitive state at 37° C. and 41° C. In contrast, under identical buffer conditions glycerol treatment did not prevent the thermolysin-mediated proteolysis of a-casein, a protein with an open and flexible conformation[38] (data not shown). The inhibitory effect of glycerol on CTA1 proteolysis was thus unlikely to result from a direct inhibition of thermolysin activity. Instead, glycerol treatment appeared to keep CTA1 in a folded, protease-resistant conformation at 37° C. and 41° C.

Effect of Glycerol on CTA1 Thermal Stability

Figure 8:
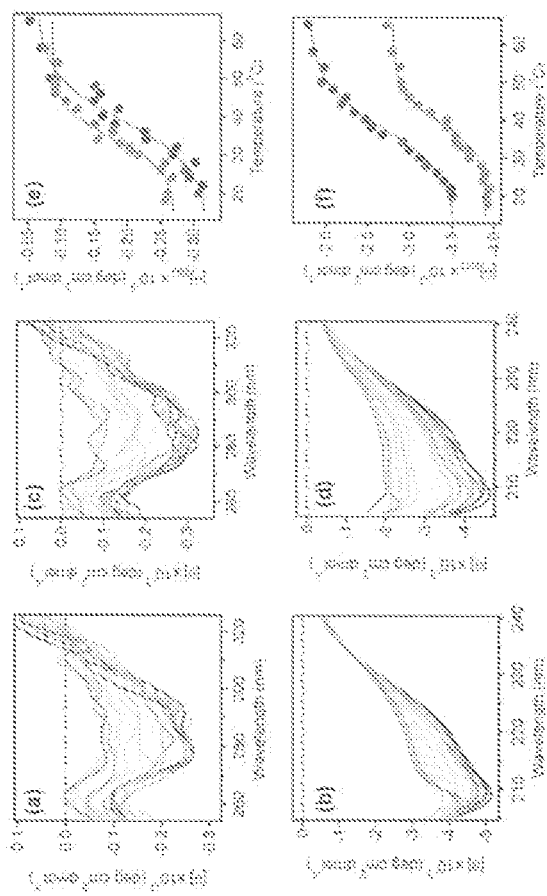

Biophysical experiments were performed in order to directly examine the impact of glycerol on CTA1 thermal instability (FIG. 8). Near- and far-UV circular dichroism (CD) measurements were conducted on His$_6$-tagged CTA1 in the absence or presence of 10% glycerol. Readings were taken during a step-wise increase in temperature from 18° C. to 65° C. Near-UV CD measurements detected the disordering of CTA1 tertiary structure (FIGS. 8(a) and 8(c)), while far-UV CD measurements detected the unfolding of CTA1 secondary structure (FIGS. 8(b) and 8(d)). To avoid errors from sample-to-sample variability, both measurements were conducted near-simultaneously on the same sample. The data from these experiments were used to generate CTA1 thermal unfolding profiles (FIGS. 8(e) and 8(f)) which were, in turn, used to calculate the amount of initial (18° C.) tertiary and secondary structure remaining in CTA1 at various temperatures (Table 1, below). The tertiary structure of CTA1 exhibited a transition temperature ($T_m$) of 34±1° C. in the untreated control condition and a $T_m$ of 39.5±1° C. in the presence of glycerol (Table 2). Untreated CTA1 only retained 33% of its initial tertiary structure at 37° C., whereas glycerol-treated CTA1 retained 58% of its initial tertiary structure at 37° C. In contrast, the thermal unfolding profile of CTA1 secondary structure was not shifted by glycerol: in both the absence and presence of 10% glycerol, CTA1 exhibited a secondary structure $T_m$ of 39±0.5° C. and retained ~60% of its initial secondary structure at 37° C. These data delineate a significant effect of glycerol on the heat-sensitivity of CTA1 tertiary structure. The thermal disordering of CTA1 tertiary structure normally preceded the perturbation of CTA1 secondary structure,[24] but in the presence of 10% glycerol the temperature-induced loss of CTA1 tertiary structure was shifted to higher temperatures and occurred in parallel with the loss of CTA1 secondary structure. Thus, glycerol treatment preferentially increased the thermal stability of the tertiary structure of CTA1 while exerting little effect on the secondary structure of the protein.

Effect of Glycerol on CTA1 Dislocation

According to our model, the thermal stabilization of CTA1 should block its export to the cytosol. A previously described assay[28] for monitoring CTA1 dislocation from the ER was used to test this prediction (FIG. 9(a)). HeLa cells incubated on ice for 30 minutes with 1 mg/ml of CT were chased for 2 hours at 37° C. in toxin-free medium that lacked or contained 10% glycerol. Previous studies have demonstrated that glycerol equilibrates across the plasma membrane with a $t_{1/2}$ of 5 minutes,[32] while it takes about 45 minutes for a fraction of surface-bound CT to reach the ER.[5,16] Selective permeabilization of the plasma membrane with digitonin was used to partition the toxin-treated cells into two fractions that contained either (i) the plasma membrane and intact intracellular membranes or (ii) the cytosol. Control experiments demonstrated that protein disulfide isomerase (PDI), a soluble ER protein, was only found in the pellet fractions (i.e., ER and other membranes) of untreated and glycerol-treated cells. Furthermore, the cytosolic protein Hsp90 was found in the supernatant fractions (i.e., cytosol) of both untreated and glycerol-treated cells. Our fractionation procedure could thus clearly separate cell extracts into distinct organelle and cytosolic components. CTA1 was only detected in the pellet fraction after pulse labeling at 4° C., a temperature that blocks the endocytosis of surface-bound protein. However, as expected, a portion of surface-bound CTA1 entered the cytosolic fraction after a 2 hour chase at 37° C. Less CTA1 was found in the cytosol of glycerol-treated cells than in the cytosol of untreated control cells (FIG. 9(a)). Semi-quantitative analysis of our dislocation assay indicated that 23±8% of the total cellular pool of CTA1 was present in the cytosolic fraction of untreated cells, and 7±4% of the total cellular pool of CTA1 was present in the cytosolic fraction of glycerol-treated cells (n=2). In the two individual experiments, glycerol treatment resulted in a 3-fold or 5-fold reduction in cytosolic CTA1. This indicated that the glycerol-induced stabilization of CTA1 tertiary structure inhibited CTA1 dislocation into the cytosol.

Figure 9:
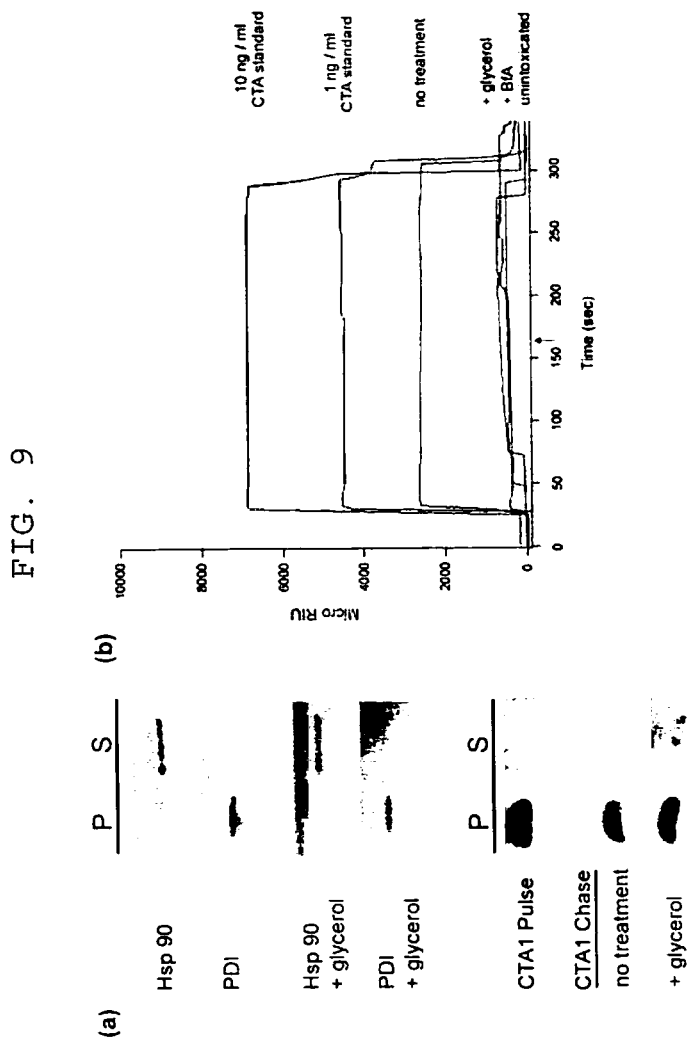
Figure 15:
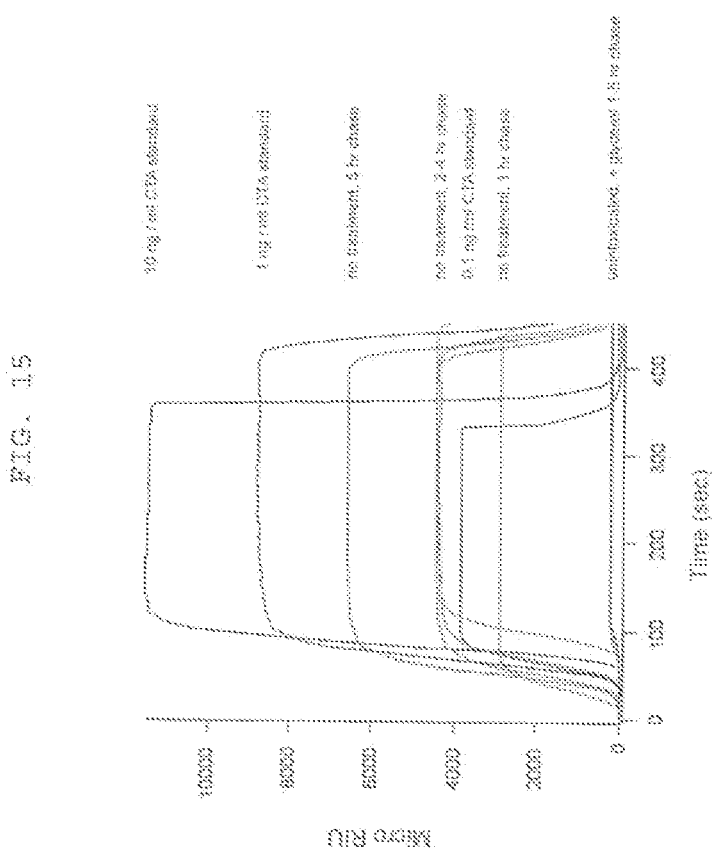
FIG. 15 shows how glycerol blocks the time-dependent appearance of CTA1 in the cytosol; HeLa cells were pulse-labeled at 4° C. for 30 min with 1 mg/ml of CT; the cells were then chased for 1, 2, 3, 4, or 5 hr at 37° C. in toxin-free medium that lacked or contained 10% glycerol; selective permeabilization of the plasma membrane with digitonin was used to partition cell extracts into separate membrane and cytosolic fractions; an SPR sensor slide coated with an anti-CTA antibody was used to detect the cytosolic pools of CTA1 from untreated (green lines) or glycerol-treated (red lines); CTA standards (10 ng/ml, 1 ng/ml, and 0.1 ng/ml; black lines) were perfused over the sensor slide as positive controls; a cytosolic fraction from unintoxicated cells (blue line) was also generated for this experiment; a small pool of CTA1 was detected in the cytosol of untreated cells after 1 hr of chase; the amount of cytosolic CTA1 increased after 2 hr of chase and remained constant over 3 and 4 hr of chase; after five hours of chase, an additional increase in cytosolic CTA1 was detected; no cytosolic pool of CTA1 was detected at any time point for the glycerol-treated cells; at the end of each experiment, bound sample was stripped from the sensor slide with a PBST wash at pH 6.0.

Surface plasmon resonance (SPR) was used as an alternative method to detect the cytosolic pool of CTA1 (FIG. 9(b)). Cytosolic fractions from intoxicated HeLa cells were prepared as described above and perfused over an SPR sensor slide that was coated with an anti-CTA antibody. No signal was obtained from the cytosol of unintoxicated HeLa cells and from the cytosol of intoxicated cells treated with brefeldin A (BfA), a drug that blocks toxin trafficking to the ER dislocation site.[5,39] Cells intoxicated in the presence of 10% glycerol also failed to generate a positive cytosolic signal for CTA1 (n=4). In contrast, we could reproducibly detect the cytosolic pool of CTA1 from intoxicated but otherwise untreated control cells. When this assay was repeated as a five hour time course experiment, we recorded a time-dependent increase in the cytosolic pool of CTA1. However, CTA1 could not be detected in the cytosol of glycerol-treated cells at 1, 2, 3, 4, or 5 hours of chase (FIG. 15). The apparent discrepancy between this result and the result presented for Western blot analysis of toxin dislocation, in which a minor pool of CTA1 was detected in the cytosol of glycerol-treated cells (FIG. 9(a)), stems from a procedural difference in the detection methods. For SPR analysis, the cytosolic fractions had to be diluted in order to obtain a sufficient volume of sample to run through the SPR instrument. This process apparently diluted the cytosolic pool of CTA1 from glycerol-treated cells to a level below the threshold of detection for SPR. However, both SPR and Western blot analysis recorded the same qualitative effect: less CTA1 was found in the cytosol of glycerol-treated cells than in the cytosol of untreated control cells. These collective observations provided additional support for our conclusion that the glycerol-induced thermal stabilization of CTA1 prevented toxin dislocation to the cytosol.

Effect of Glycerol on CTA1 Secretion from Intoxicated Cells

Figure 10:
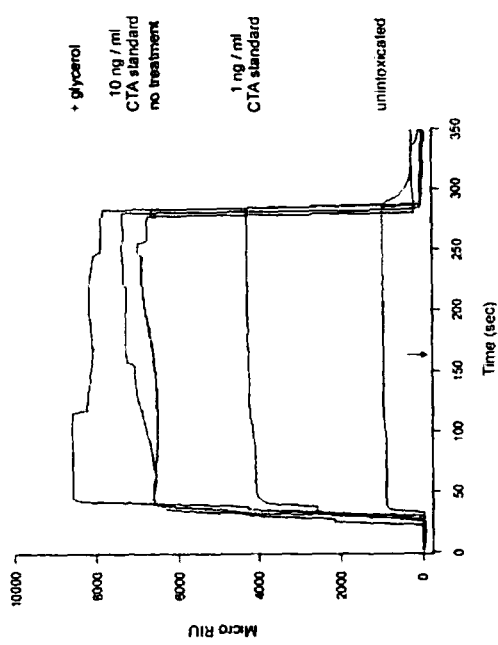
Figure 16:
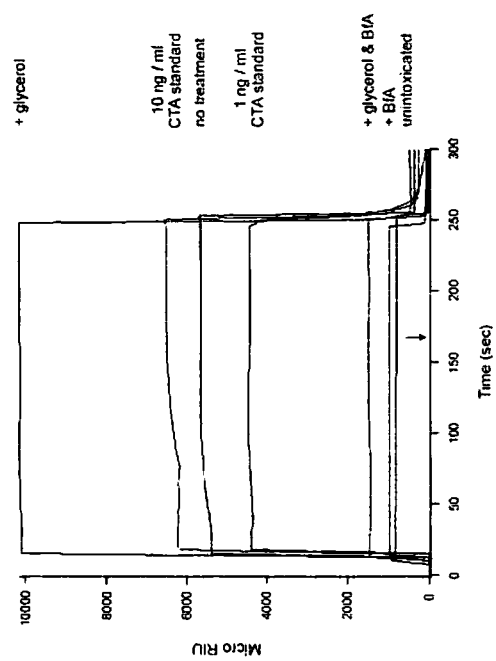
FIG. 16 shows CTA1 secretion from Vero cells; Vero cells pulse-labeled at 4° C. for 30 min with 1 mg/ml of CT were chased for 2 hr at 37° C. in toxin-free medium that lacked (no treatment) or contained 10% glycerol (+glycerol); a separate set of intoxicated cells were chased in medium that contained either 5 mg/ml of BfA (+BfA) or both 10% glycerol and 5 mg/ml of BfA (+glycerol & BfA); media samples from the intoxicated cells and from unintoxicated control cells were then analyzed by SPR with a sensor slide that had been coated with an anti-CTA antibody; CTA standards (10 ng/ml and 1 ng/ml) were also perfused over the sensor slide as positive controls; the arrow indicates when the sample was removed from the perfusion buffer; at the end of each experiment, bound sample was stripped from the sensor slide with a 5 min PBST wash at pH 6.0.

Misfolded or misassembled proteins and proteins with specific targeting determinants are effectively retained in the ER; all other proteins are packaged into vesicle carriers for transport to the Golgi apparatus and beyond.[14] Stabilization of the CTA1 tertiary structure could therefore generate a folded toxin conformation that is recognized as secretory cargo and accordingly directed to vesicle traffic in the biosynthetic secretory pathway. In this case, glycerol treatment would result in the secretion of CTA1 from intoxicated cells. To examine this possibility, SPR was used to detect CTA1 in the extracellular medium of cells intoxicated in the absence or presence of 10% glycerol (FIG. 10). A minimal background signal was detected when the medium from unintoxicated HeLa control cells was perfused over a SPR sensor slide that had been coated with an anti-CTA antibody. A positive signal was detected when the medium from intoxicated cells was perfused over the sensor slide, and an even stronger signal was obtained from the medium of intoxicated cells incubated with 10% glycerol (FIG. 10). This indicated that, as previously reported, some amount of CTA1 was released into the medium during the normal intoxication process.[3] However, a greater amount of CTA1 was released into the medium when the toxin was stabilized by glycerol treatment (FIG. 10). No signal was detected when the experiment was performed with a sensor slide that had been coated with an anti-CTB antibody, thus demonstrating that the positive response from the CTA sensor slide did not result from the presence of CT holotoxin in the medium (data not shown). Similar results were obtained with Vero cells which, unlike HeLa cells, did not require GM1 pre-treatment before intoxication (FIG. 16). Thus, the results of the HeLa secretion assay could not be attributed to GM1 treatment or to cell-type specific effects.

Figure 11:
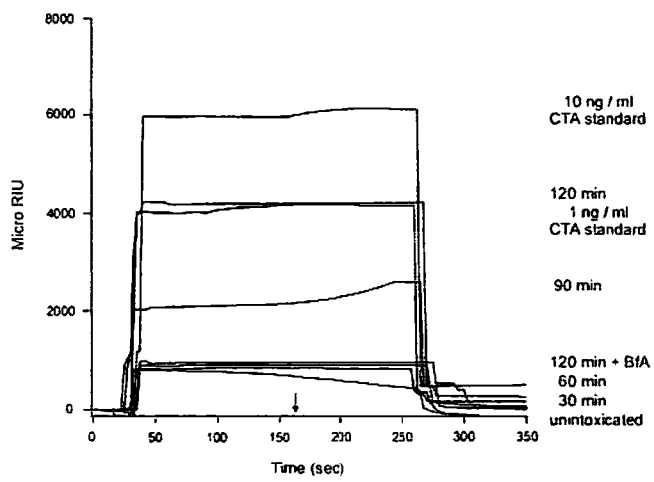
Figure 11:
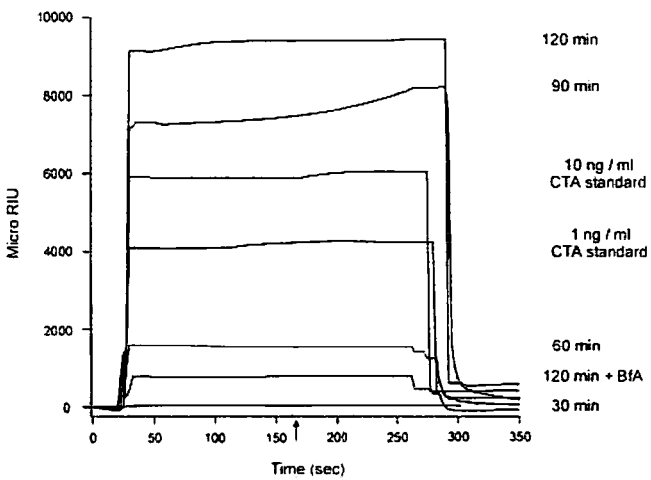
Figure 11:
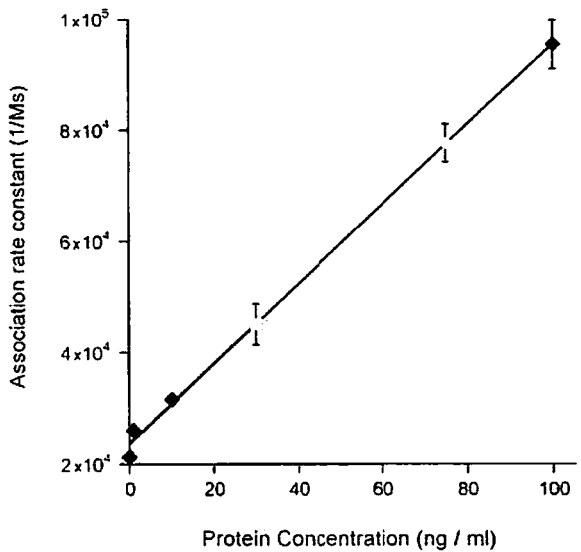

Because CTA1 dissociates from CTA2/CTB5 in the ER,[7-9] the secretion of CTA1 from glycerol-treated cells strongly suggested that 10% glycerol did not inhibit trafficking of the CT holotoxin to the ER. BfA, a drug that disrupts toxin transport to the ER,[5,39] was used to strengthen this interpretation. When the SPR secretion assay was repeated with cells exposed to BfA, we could not detect an appreciable amount of CTA1 in the medium of intoxicated cells incubated in either the absence or presence of 10% glycerol (FIGS. 11(a) and b)). Thus, toxin trafficking to the ER was a prerequisite for CTA1 secretion. The kinetics of secretion also indicated that intracellular toxin trafficking preceded the release of CTA1 into the medium: substantial amounts of extracellular CTA1 were not detected until 90 minutes into the chase period, after which a greater amount of CTA1 was released into the medium (FIGS. 11(a) and (b)). Analysis of these kinetic data and the data presented in FIG. 10 indicated that glycerol-treated cells secreted twice as much CTA1 as the untreated control cells (FIG. 11(c)). Given that only a minor fraction (~5%) of cell-associated CT reaches the ER,[5,39] a two-fold increase in CTA1 secretion from glycerol-treated cells may represent the bulk of ER-localized toxin. It thus appeared that the glycerol-stabilized pool of CTA1 was treated as secretory cargo rather than as an ERAD substrate and was accordingly released into the extracellular medium.

Effect of Glycerol on CTA1 Dissociation from the Holotoxin

Figure 12:
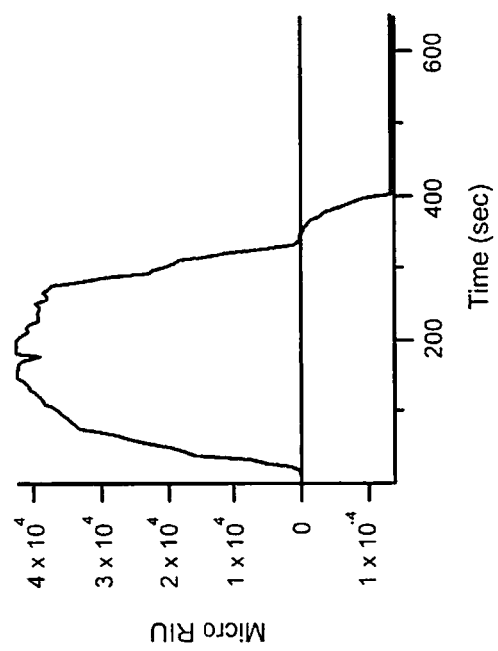

Results from the SPR secretion assays indicated that glycerol treatment did not prevent CTA1 dissociation from the holotoxin: if glycerol inhibited this event, CTA1 would be tethered to CTA2/CTB$_5$ and could not enter the extracellular medium in a soluble state. An SPR-based experiment directly confirmed that glycerol treatment did not prevent CTA1 dissociation from the holotoxin (FIG. 12). In this experiment, the CT holotoxin was appended to a GM1-coated sensor slide. Reduced PDI was then perfused over the sensor slide in the presence of 10% glycerol. Previous biochemical work has shown that reduced PDI facilitates the dissociation of CTA1 from CTA2/CTB$_5$.[9] Our SPR experiment confirmed this PDI-mediated event also occurs in the presence of 10% glycerol. Reduced PDI bound to CT and accordingly generated an increase in the measured refractive index. Although PDI was present in the perfusion buffer throughout the experiment, the refractive index began to drop precipitously 290 seconds into the experiments and eventually fell below the initial baseline value which represented the mass of the CT holotoxin. It thus appeared that both PDI and a component of the CT holotoxin were removed from the sensor slide. This would occur if PDI facilitated the dissociation of CTA1 from CTA2/CTB$_5$: since the B pentamer was bound to the sensor slide, the release of CTA1 from the holotoxin would wash both PDI and CTA1 off the plate. To confirm that CTA1 was removed from the sensor-bound toxin, we perfused an anti-CTA antibody over the sensor slide. No signal was obtained with the anti-CTA antibody, thus indicating that CTA1 was absent from the PDI-treated toxin. In contrast, the anti-CTA antibody generated a robust signal when perfused over a sensor slide containing the intact CT holotoxin (data not shown).[24] Additional control experiments with anti-CTB, anti-KDEL, or anti-PDI antibodies demonstrated that CTB and the KDEL-tagged CTA2 subunit, but not PDI, remained on the SPR sensor slide after the loss of CTA1 (data not shown).

Effect of Glycerol on CT Intoxication

Figure 13:
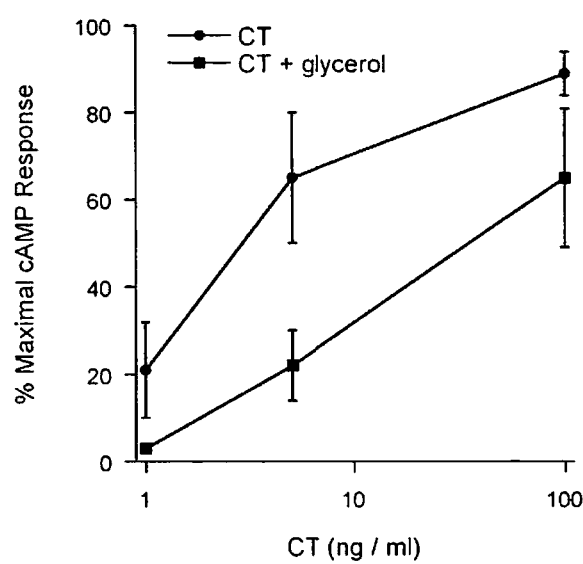

The glycerol-induced block of CTA1 dislocation into the cytosol should prevent productive CT intoxication. To test this prediction, we monitored cAMP levels in untreated and glycerol-treated cells that had been continually exposed to varying concentrations of CT for 2 hours (FIG. 13).

Glycerol-treated cells were indeed resistant to CT. Whereas a 50% maximal response was obtained with 3 ng of CT/ml in the untreated control cells, 35 ng of CT/ml was required to elicit the same effect in glycerol-treated cells. This effect was most likely due to direct inhibition of the CT intoxication process, as control experiments found that glycerol did not inhibit forskolin-stimulated adenylate cyclase activity: cells treated with glycerol and forskolin produced 105% of the cAMP signal generated by cells treated with forskolin alone. Furthermore, our SPR experiments demonstrated that glycerol treatment did not prevent CT trafficking to the ER or CTA1 dissociation from the holotoxin. Thus, the glycerol-induced inhibition of CT intoxication most likely resulted from the glycerol-induced block of CTA1 dislocation to the cytosol.

Effect of Glycerol on CTA1 Degradation by the 20S Proteasome

Figure 14:
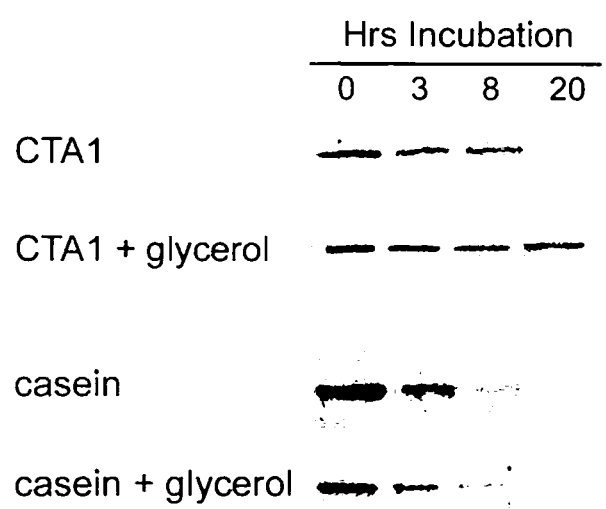
FIG. 14 presents data that glycerol inhibits CTA1 degradation by the 20S proteasome; (a): reduced CTA1/CTA2 heterodimers were incubated at 37° C. with 100 nM of the 20S proteasome in the absence or presence of 10% glycerol; samples taken at the indicated time points were visualized by SDS-PAGE and Coomassie staining; (b): an identical protocol was followed with a-casein as the sample protein.

CTA1 is an in vitro substrate for ubiquitin-independent degradation by the 20S proteasome.[24] This macromolecular complex forms the catalytic core of the 26S proteasome, which is generated by the addition of a 19S cap to one or both ends of the barrel-shaped 20S proteasome. The function of the 19S regulatory domain is ubiquitin recognition and ATP-dependent substrate unfolding, so the core 20S proteasome can only degrade a limited number of unfolded proteins in a ubiquitin- and ATP-independent process.[29] To determine whether the stabilization of CTA1 tertiary structure inhibited toxin degradation by the 20S proteasome, we incubated a reduced CTA1/CTA2 heterodimer with the purified 20S proteasome for up to 20 hours in the absence or presence of 10% glycerol (FIG. 14(a)). Degradation of the reduced, isolated CTA1 subunit by the 20S proteasome was detected after 3 hours of co-incubation in our control condition and was nearly complete by 20 hours of co-incubation. However, substantial inhibition of CTA1 degradation by the 20S proteasome was observed when the toxin was incubated with both 10% glycerol and the 20S proteasome. Glycerol did not inhibit a-casein degradation by the 20S proteasome (FIG. 14(b)), which demonstrated that 10% glycerol did not directly impair the in vitro activity of the core 20S proteasome. The stabilization of CTA1 tertiary structure by glycerol thus prevented its ubiquitin-independent degradation by the 20S proteasome.

Discussion

Toxin-ERAD interactions were originally thought to involve the C-terminal hydrophobic region of CTA1, but recent work has shown that this domain is not required for CTA1 dislocation.[22] An alternative ERAD trigger could derive from the unstable, heat-labile nature of the isolated CTA1 polypeptide.[23,24] With this model, the global loss of CTA1 structure that accompanies its dissociation from the holotoxin would identify it as a misfolded protein for ERAD processing. We accordingly predicted that the thermal stabilization of CTA1 would prevent its export to the cytosol and, hence, productive intoxication. The results of our experiments with glycerol-treated cells, combined with biophysical studies on purified proteins, support this prediction. Our findings identify the thermal unfolding of CTA1 tertiary structure as a requirement for ERAD recognition and thus provide a novel molecular mechanism for ERAD-mediated CTA1 dislocation.

The thermal disordering of CTA1 tertiary structure normally preceded the thermal denaturation of CTA1 secondary structure by 5-6° C.[24] However, here we show that in the presence of 10% glycerol the loss of CTA1 tertiary structure was shifted to higher temperatures and occurred concomitantly with the loss of CTA1 secondary structure. Glycerol did not affect the thermal perturbation of CTA1 secondary structure, so the glycerol-induced effects on toxin processing apparently resulted from the specific stabilization of CTA1 tertiary structure.

The near-UV CD signal around 280 nm that was used to track changes in CTA1 tertiary structure involves contributions from both Trp and Tyr residues. Two of the three CTA1 Trp residues that make substantial contributions to the near-UV CD signal are present in the C-terminal domain that has previously been shown to be in a partially unfolded state. The glycerol-induced stabilization of CTA1 tertiary structure may therefore involve an effect on the C-terminal A1$_3$ subdomain. In this scenario, unfolding of the CTA1 C-terminus would precede the loss of additional structure in the remainder of the toxin. Since the A1$_3$ subdomain is not necessary for CTA1 dislocation, the temperature-induced loss of structure in other regions of CTA1 would serve as the ERAD trigger. This possibility is consistent with our interpretation of the available data—namely, that the thermal unfolding of CTA1 tertiary structure is required to activate the ERAD system. Additional structural studies will delineate the process of CTA1 thermal unfolding which begins with the loss of tertiary structure. Here, we focused on the disruption of host-toxin interactions resulting from the glycerol-induced stabilization of CTA1 tertiary structure.

Control conditions ensured that the glycerol-induced effects were due to the impact of glycerol on CTA1 structure rather than to the action of glycerol on other components of the experiment. For example, we used a-casein, a protein with a flexible and open structure,[38] to demonstrate that glycerol did not directly inhibit the proteolytic activities of thermolysin or the 20S proteasome. Additional experiments demonstrated that glycerol treatment did not disrupt (i) holotoxin trafficking to the ER; (ii) chaperone-assisted dissociation of CTA1 from CTA2/CTB$_5$; (iii) secretion of the dissociated CTA1 subunit; or (iv) cAMP production from activated adenylate cyclase. Other studies have further shown that glycerol treatment does not affect the vesicular transport of secretory cargo, N-linked glycosylation in the endomembrane system, the functioning of chloride channels, or the ERAD-independent ER dislocation of the A subunit from *Haemophilus ducreyi* cytolethal distending toxin.[32-34,40] Thus, the impact of glycerol on CTA1 processing is highly unlikely to result from generic cellular effects. It instead appears to have resulted specifically from the stabilization of CTA1 tertiary structure.

There is one established case in which glycerol treatment does have a general effect on cellular events: chemical chaperones such as glycerol stabilize the folding intermediates in protein biogenesis, and this has been shown to alter the processing of many ERAD substrates.[30-34] CTA1 therefore acts as a typical misfolded/unfolded ERAD substrate, which contradicts a prevailing model of toxin-ERAD interactions that treats CTA1 as a stable protein.[6,9,18,18,28]

Glycerol treatment did not prevent CT trafficking to the ER or CTA1 dissociation from the holotoxin. However, glycerol treatment did prevent the ER-to-cytosol dislocation of CTA1. CT intoxication was consequently impaired in glycerol-treated cells. These effects, which specifically resulted from the stabilization of CTA1 tertiary structure, demonstrated the functional consequences of CTA1 thermal stabilization. The trigger for ERAD-mediated dislocation thus appears to derive from a global loss of CTA1 tertiary structure rather than from the presence of a specific domain or motif within the toxin. As such, CTA1 does not masquerade as misfolded protein to activate the ERAD system. CTA1 is instead recognized as an ERAD substrate because, upon holotoxin disassembly, the thermal disordering of its tertiary structure produces an unfolded toxin conformation.

The thermal stabilization of CTA1 blocked its ERAD-mediated dislocation to the cytosol and instead promoted its secretion into the extracellular medium. This suggested that the stabilized pool of CTA1 was not retained in the ER of glycerol-treated cells but was instead treated as normal secretory cargo and released into the medium. A relatively small portion of cell-associated CT (~5%) reaches the ER,[5,39] so the two-fold increase in CTA1 secretion from glycerol-treated cells may represent the bulk of ER-localized toxin. Since the secreted pool of CTA1 was not linked to its cell-binding B subunit, it could not reassociate with target cells and was therefore functionally inactive. The release of CTA1 from glycerol-treated cells would also prevent its accumulation in the ER and any resulting ER stress response. Given these considerations, it appears that A chain thermal stabilization is a promising anti-toxin therapeutic strategy.

CTA1 is degraded in vivo by a relatively slow, ubiquitin-independent proteasomal mechanism. This process likely involves the core 20S proteasome, which can degrade CTA1 in an ATP- and ubiquitin-independent manner in vitro.[24] The glycerol-induced inhibition of CTA1 degradation by the 20S proteasome indicated that the loss of toxin tertiary structure is responsible for targeting CTA1 to the 20S proteasome. This interpretation is consistent with a previous report that concluded the 20S proteasome recognizes substrates with disordered tertiary structures.[41] Collectively, these data suggest that CTA1 degradation in the host cell cytosol results from the thermal disordering of CTA1 tertiary structure. The slow rate of CTA1 turnover in vivo, which under normal circumstances does not impact intoxication,[18] most likely reflects inefficient processing by the 20S variant of the proteasome and/or CTA1 association with stabilizing host proteins such as the ADP-ribosylation factors.[23,24]

Our collective data indicate that CTA1 thermal instability plays an essential role in the intoxication process. Thus, the thermal stabilization of CTA1 is a novel target for anti-toxin therapeutics. We have provided proof-of-principle for this concept by demonstrating that the glycerol-induced stabilization of CTA1 tertiary structure blocks toxin dislocation from the ER and productive intoxication. Exposure to high concentrations of glycerol is not a viable therapeutic option, but other chemical chaperones or target-specific "pharmacological chaperones" can stabilize protein conformations without toxic side-effects.[42] Other ER-dislocating toxins also contain thermally unstable A chains,[37,43,44] so the use of chemical or pharmacological chaperones for toxin thermal stabilization may represent a new, general strategy for anti-toxin treatments.

Materials and Methods

Chemicals, thermolysin, a-casein, rabbit anti-CTA antibody, and ganglioside GM1 were purchased from Sigma-Aldrich (St. Louis, Mo.). CT was purchased from List Biological Laboratories (Campbell, Calif.). Cell culture reagents were purchased from Invitrogen (Carlsbad, Calif.). ATP and the purified CTA1/CTA2 heterodimer were purchased from Calbiochem (La Jolla, Calif.). The purified 20S proteasome was from Boston Biochem (Cambridge, Mass.). [$^{35}$S]methionine was purchased from Perkin-Elmer (Boston, Mass.). Rabbit anti-Hsp90 and anti-PDI antibodies were purchased from Stressgen Bioreagents Corp. (Victoria, BC Canada); the horseradish peroxidase-conjugated goat anti-rabbit IgG antibody was from Jackson Immunoresearch Laboratories Inc. (West Grove Pa.); and Talon beads were from Clontech Laboratories (Mountain View, Calif.).

Protease Sensitivity Assay

A master mix containing 6 mg of CTA1/CTA2, 10 mM 6-ME, and 20 mM sodium phosphate (pH 7.0) was prepared in a volume of 120 ml. A second master mix was prepared as above but with a final concentration of 10% glycerol. The mixes were divided into 20 ml aliquots and incubated at 4° C., 25° C., 33° C., 37° C., or 41° C. for 45 minutes. The aliquots were then placed on ice for 10 minutes, after which 2 ml of thermolysin was added to all the samples for a 1 hour incubation at 4° C. Thermolysin, prepared as a 10×stock in 50 mM CaCl$_2$ and 100 mM Hepes (pH 8.0), was added to a final concentration of 0.04 mg/ml. Digestions were halted by the addition of ethylenediaminetetraacetic acid (EDTA) to a final concentration of 10 mM. Samples were analyzed by SDS-PAGE with 15% polyacrylamide gels. Coomassie staining was used to visualize the samples.

CTA1-His6 Purification

*Escherichia coli* strain BL21 pLysS was transformed with an inducible CTA1-His$_6$ expression plasmid[22] and grown at 37° C. in 1 liter Luria-Bertani broth to an A$_{600}$ of 0.6. CTA1-His$_6$ expression was induced by addition of 1 mM IPTG to the growth medium. The cells were pelleted after 4 hrs of induction, resuspended in extraction buffer (20 mM Tris-HCl, pH 7.0, 300 mM NaCl, 0.1% Triton X-100, 1% deoxycholate, 100 mg/ml of lysozyme, and 8 M urea), and lysed with three freeze-thaw cycles. The insoluble lysate fraction was removed with a 30 min, 12,000×g spin. The soluble fraction was then supplemented with a protease inhibitor cocktail and incubated in batch with Talon resin for 30 min at room temperature. Unbound material in the supernatant was removed with a 5 min spin at 700×g, and the resin was washed four times with extraction buffer containing 600 mM NaCl. To elute the bound toxin, the resin was placed in a column and exposed to increasing concentrations of imidazole in extraction buffer (10, 15, 20, 25, 35, 40, 45, and 100 mM imidazole; 2 mls for each concentration). Fractions of 0.5 ml volume were collected and analyzed by SDS-PAGE. Before experimental use, the fractions containing purified CTA1-His$_6$ were dialyzed against five changes of 500 ml sodium phosphate buffer (pH 7.4) in order to facilitate the refolding of CTA1: the first step was for 2 hr at room temperature in 6 M urea buffer; the second step was overnight at 4° C. in 4 M urea buffer; the third step was for 2 hrs at 4° C. in 2 M urea buffer; the fourth step was for 1 hr at 4° C. in urea-free buffer; and the last step was for 20 min at 4° C. in urea-free buffer. Slide-a-lyzer 3500 MWCO dialysis cups (Pierce, Rockford, Ill.) were used for the procedure. After dialysis, CTA1-$His_6$ was used immediately for experimentation.

CD Measurements

A J-810 spectrofluoropolarimeter (Jasco Corp., Tokyo, Japan) with a Jasco PFD-425S Peltier temperature controller was used to study the temperature-dependent unfolding of CTA1-$His_6$. Near- and far-UV CD measurements were performed with a 4-mm optical path-length rectangular quartz cuvette at a protein concentration of 73 mg/ml in 20 mM sodium borate buffer (pH 7.4) containing 150 mM NaCl. Thermal unfolding was carried out in the temperature range of 18-65° C. Samples were equilibrated for 4 minutes at each temperature, followed by measurements of CD spectra from 195 to 325 nm. Five scans were recorded and averaged per spectrum. The observed ellipticity was converted to mean residue molar ellipticity, [θ], in units of degrees×$cm^2$×$dmol^{-1}$ using $[\theta]=\theta_{obs}/cn_{res}l$, where $\theta_{obs}$ is the measured ellipticity in millidegrees, c is the molar concentration of the protein, $n_{res}$ is the number of amino acid residues in the protein, and l is the optical path-length in millimeters. The temperature-dependent protein unfolding data were analyzed as previously described.[24] The thermal unfolding profiles for TA1-$His_6$ were nearly identical to the profiles reported for native CTA1, which in the reduced state exhibited a secondary structure $T_m$ of 37.5° C. and a tertiary structure $T_m$ of 32° C.[24]

The change in the near-UV CD signal at 280 nm reflects two things: the local environment of Trp and Tyr residues, and the conformation of the side chains of these residues. Changes in the local environment are caused by changes in the protein tertiary structure. A more tightly packed tertiary structure brings the main chain Cα atoms closer to the aromatic side chains and makes their local environment more chiral, thus affecting the aromatic side chain CD signal. As such, the changes in the near-UV CD signal around 280 nm reflect (i) changes in the local environment of Trp and Tyr residues and, thus, the protein tertiary structure; and (ii) the conformations of Trp and Tyr side chains. We accordingly interpreted the changes in this signal in terms of protein tertiary structure.

Dislocation and Secretion Assays

HeLa cells were seeded into 6 well plates and grown overnight to a density of approximately 10,000 cells/well. Duplicate wells were used for each condition. To begin the experiment, the cells were incubated for 1 hour at 37° C. in serum-free medium containing 100 ng/ml of ganglioside GM1. This medium was subsequently replaced with serum-free medium containing 1 mg/ml of CT. After a 30 minute incubation at 4° C., the cells were washed twice with phosphate buffered saline (PBS) and placed in toxin/serum-free medium that either lacked or contained 10% glycerol. The cells were then incubated for 2 hours at 37° C. Media samples were collected for analysis by SPR, and cells were lifted from the plate using 750 ml of 0.5 mM EDTA in PBS. Both wells for each condition were added to a single microcentrifuge tube which was spun at 5,000×g for 5 minutes at room temperature. The supernatant was discarded, and the cell pellet was resuspended in 100 ml of 0.04% digitonin in HCN buffer (50 mM HEPES, pH 7.5, 150 mM NaCl, 2 mM $CaCl_2$, 10 mM N-ethylmaleimide, and a protease inhibitor cocktail) for a 10 minute incubation at 4° C. The digitonin-treated cells were spun at 16,000×g for 10 minutes at room temperature, after which the supernatant (i.e., cytosolic fraction) was collected and placed in a fresh microcentrifuge tube. For experiments involving Western blot analysis, 120 ml of 1× sample buffer was added to the pellet and 20 ml of 4× sample buffer was added to the supernatant.

Western Blot 25 ml samples resolved by SDS-PAGE with 15% polyacrylamide gels were subsequently transferred to a PVDF membrane. The membrane was incubated overnight at 4° C. with primary antibody (rabbit anti-Hsp90 at 1:20,000 dilution; rabbit anti-PDI at 1:5,000 dilution; or rabbit anti-CTA at 1:20,000 dilution). The membrane was then incubated at room temperature for 30 minutes with a secondary antibody (horseradish peroxidase-conjugated goat anti-rabbit IgG at 1:20,000 dilution). ECL Plus Western blotting detection reagents (GE Healthcare) were used for protein detection according to the manufacturer's instructions. Separate blots were run for each protein.

For semi-quantitative analysis of our dislocation assay, the amount of cytosolic CTA1 was calculated with the following equation: % cytosolic CTA1=CTA1 supernatant signal/[CTA1 supernatant signal+CTA1 pellet signal]. This calculation provides an internal control, as the amount of cytosolic CTA1 is expressed as a ratio of total cell-associated CTA1 for each experimental condition. Thus, there is no direct comparison of band intensities between separate cell extracts representing control and experimental conditions (i.e., +/−glycerol treatment).

SPR Analysis

Experiments were performed with a Reichert (Depew, N.Y.) SR7000 SPR Refractometer. To generate sensor slides coated with an anti-CTA antibody, an EDC-NHS activation buffer was perfused over a Reichert gold-plated glass slide for 10 min at a flow rate of 5 ml/min. The same flow rate was used for all steps of the procedure. A 5 min wash with PBS (pH 7.4) containing 1% Triton X-100 (PBST) was used to remove the activation buffer, after which an anti-CTA antibody at 1:2000 dilution in PBST was perfused over the slide for 15 min. Unbound antibody was removed with a 5 min PBST wash, and the remaining active groups on the sensor slide were deactivated with a 3 min exposure to ethanolamine.

To detect the cytosolic or secreted pools of CTA1, PBST (pH 7.4) was perfused over the CTA sensor slide for 5 min to establish a baseline reading. Experimental samples were then flowed over the sensor slide. Before use, cytosolic fractions from the dislocation assay were diluted in HCN buffer to a final volume of 1 ml. This step was necessary in order to obtain a sufficient volume of sample to run through the SPR instrument. For the secretion assay, all media samples were standardized to a final concentration of 5% glycerol (2 ml final volume) in order to eliminate any differential effect glycerol might have on detection by the SPR instrument. CTA standards diluted in HCN buffer or 5% glycerol were used for the dislocation assay and secretion assay, respectively. Identical results were obtained for CTA standards diluted in either HCN buffer or HCN buffer containing cellular extracts generated from unintoxicated cells (data not shown); this demonstrated that the data obtained from our dislocation assay were not affected by the presence of cytosol. Experimental samples were removed from the perfusion buffer after exposure to the SPR sensor for approximately 180 sec. This process usually results in a loss of signal which reflects the dissociation rate constant. However, for these experiments, the strong antibody-antigen interaction prevented any significant loss of signal due to ligand dissociation. After each reading, bound ligand was stripped from the sensor slide with a 5 min PBST wash at pH 6.0. The Reichert Labview software was used for data collection.

Preliminary experiments found that the pellet fractions from our dislocation assay produced SPR signals that were off-scale in relation to the weaker signals from the cytosolic fractions. We therefore focused on the relative signal intensities of the cytosolic fractions. The disparity between organelle and cytosol signals for CTA1 was consistent with the small fraction of cell-associated CTA1 (~5%) that reaches the ER and, subsequently, the cytosol.[5,39] An additional control experiment demonstrated that the cytosolic fractions did not contain a factor that inhibited the detection of CTA1: nearly identical SPR signals were obtained from 10 ng/ml of CTA in buffer and from 10 ng/ml of CTA that had been added to a cytosolic fraction obtained from unintoxicated HeLa cells.

Figure 4:
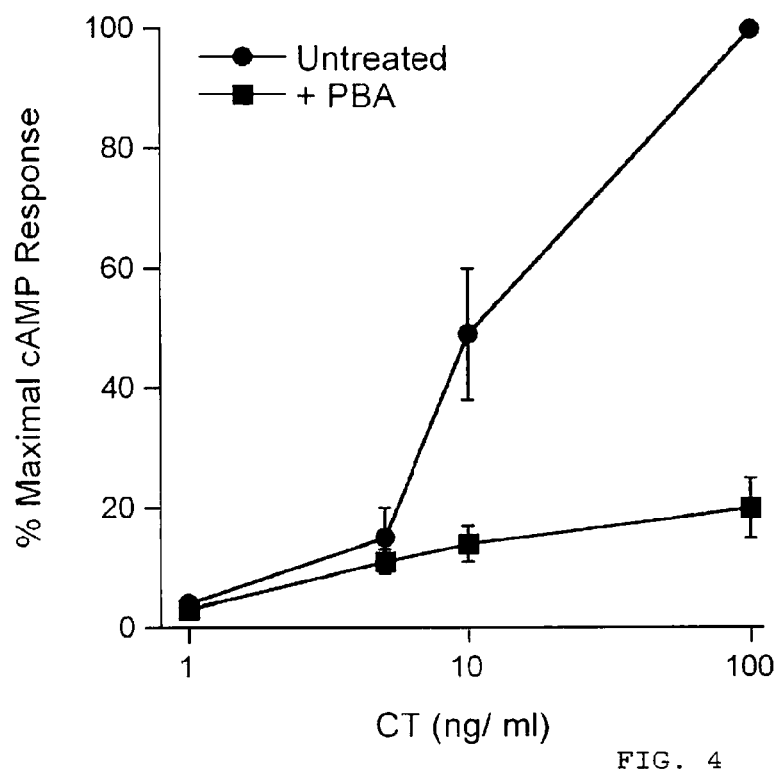
FIG. 4 provides the same comparison as FIG. 3, except the CT conc samples) are expressed as percentages of the maximal CT response for all tested conditions.
Figure 5:
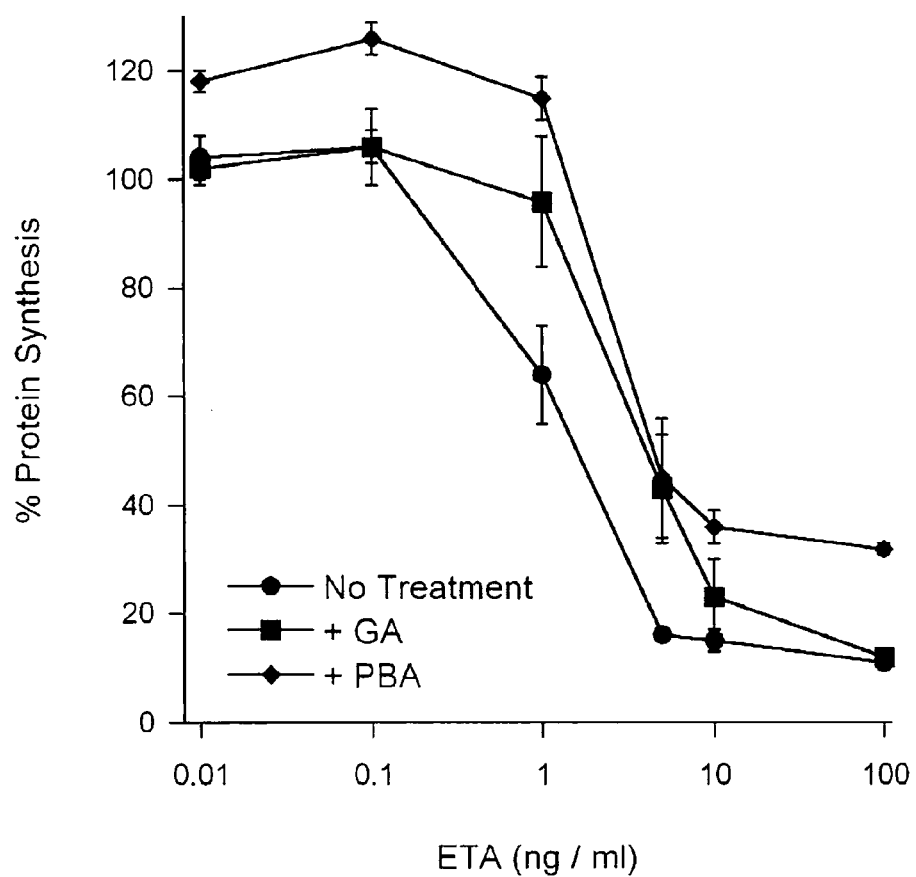
Figure 6:
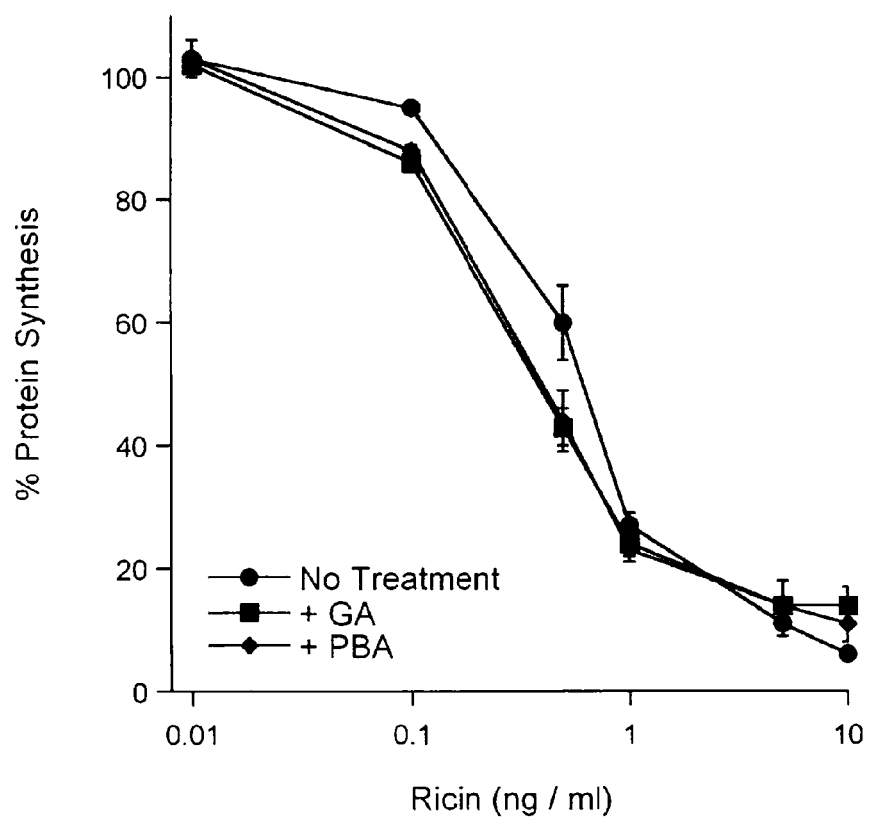

The association rate constant derived from SPR data is directly proportional to ligand concentration.[45] Thus, to determine the amount of CTA1 secreted from intoxicated cells, association rate constants were calculated for the SPR data obtained from the experimental samples of FIG. 4, from the 120 min experimental samples from FIGS. 5(a) and 5(b), and from the ten-fold serial dilutions of purified CTA that were perfused over the sensor slide as controls for FIGS. 4 and 5. The BioLogic (Campbell, Australia) Scrubber 2 software was used to derive the association rate constants from our SPR data. The association rate constants for the CTA standards were plotted as a function of protein concentration. The slope of the resulting standard curve was then used to calculate the concentrations of CTA1 in untreated and glycerol-treated media samples.

For SPR experiments using PDI and the CT holotoxin, a gold plate sensor was coated with the GM1 ganglioside receptor of CT by a procedure described for the coating of ELISA plates.[46] CT was then bound to the GM1-coated sensor by perfusing 1 ml of CT (10 mg/ml) over the slide for 15 min at a flow rate of 5 ml/min. The CT sensor was equilibrated at 37° C. in PBST and 10% glycerol for 10 min at a flow rate of 45 ml/min. The SPR instrument was then calibrated with a baseline measurement corresponding to the mass of the bound CT holotoxin. PDI was subsequently perfused over the sensor at a flow rate of 45 ml/min. PDI was diluted to a final concentration of 100 mM in PBST containing 10% glycerol and 1 mM GSH. After 420 seconds, the PDI injection was replaced with an identical PDI buffer that also contained 80 mM of an anti-CTA antibody. This PDI/antibody mixture was perfused over the sensor slide at a flow rate of 45 ml/min for 420 seconds. Control experiments demonstrated that holotoxin disassembly did not occur upon exposure to either 1 mM GSH alone or to PDI in the absence of GSH.

Toxicity Assay

CHO cells were seeded into 24 well plates and grown overnight to 80% confluency. The medium was removed and replaced with serum-free medium containing the stated concentrations of CT in the absence or presence of 10% glycerol. After a 2 hour incubation, the cells were washed with PBS and exposed to 0.25 mL of ice-cold acidic ethanol (1 M HCl: 100% EtOH at a 1:100 ratio) for 15 minutes at 4° C. The cell extracts were then transferred to microcentrifuge tubes and allowed to air dry at room temperature. cAMP levels were determined using an [$^{125}$I]cAMP competition assay as per manufacturer's instructions (Amersham Biosciences). The basal levels of cAMP determined from unintoxicated cells were background-subtracted from the values obtained for toxin-treated cells; the maximal response from all conditions was arbitrarily set to 100%; and all other results were expressed as ratios of that 100% value. All conditions were performed in triplicate.

20S Proteasome Assay

A 100 ml master mix was prepared with 1 µg 20S proteasome, 5 µg substrate, 3 mM ATP, 10 mM β-ME, 10 mM $MgCl_2$, 100 mM KCl, 0.1 mM $CaCl_2$, and 50 mM Hepes (pH 7.5). A second master mix was prepared as above but with a final concentration of 10% glycerol. The mixtures were placed at 37° C., and 20 ml aliquots were removed at 0, 4, 8, and 20 hours of incubation. Samples were analyzed by SDS-PAGE with Coomassie staining.

Hsp90 is Required for Transfer of the Cholera Toxin A1 Subunit from the Endoplasmic Reticulum to the Cytosol Cholera toxin (CT) is an AB5 toxin that moves from the cell surface to the endoplasmic reticulum (ER) by retrograde vesicular transport. In the ER, the catalytic A1 subunit dissociates from the rest of the toxin and enters the cytosol by exploiting the quality control system of ER-associated degradation (ERAD). The driving force for CTA1 dislocation into the cytosol is unknown. Here, we demonstrate that the cytosolic chaperone Hsp90 is required for CTA1 passage into the cytosol. Hsp90 bound to CTA1 in an ATP-dependent manner that was blocked by geldanamycin (GA), an established Hsp90 inhibitor. CT activity against cultured cells was also blocked by GA, as was the ER-to-cytosol export of CTA1. Experiments using N-ethylcarboxamidoadenosine (NECA), a drug that inhibits ER-localized GRP94 but not cytosolic Hsp90, confirmed that the inhibitory effects of GA resulted specifically from the loss of Hsp90 activity. GRP94 is glucose-regulated protein of 94 kDa, a major luminal constituent of the endoplasmic reticulum and paralog of Hsp90; by amino acid homology, Grp94 is about 60% homologous and 50% identical to Hsp90a. This work establishes a functional role for Hsp90 in the ERAD-mediated dislocation of CTA1.

ERAD substrates are extracted from the ER through a mechanism that often involves the AAA ATPase Cdc48/p97. However, p97 appears to play a minimal role in CTA1 dislocation. An alternative model has proposed a ratchet mechanism which involves the spontaneous refolding of CTA1 as it enters the cytosol. Recent CTA1 structural studies do not support this model, as it has been shown that the isolated CTA1 subunit is a disordered, thermally unstable protein. Since CTA1 is in a partially unfolded conformation at 37° C., an as yet unidentified host protein must provide the driving force for CTA1 extraction from the ER.

Figure 17:
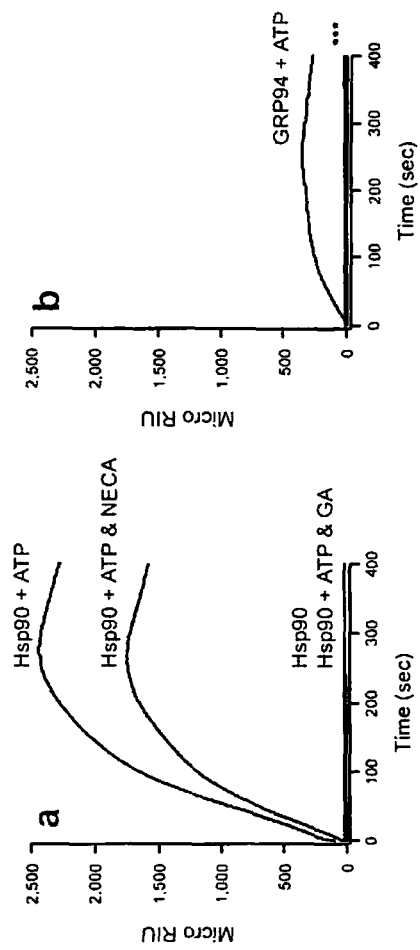
FIG. 17 indicates that GA but not N-ethylcarboxamidoadenosine (NECA) inhibits the interaction between CTA1 and Hsp90; either Hsp90 (a) or GRP94 (b) was perfused over a CTA1-coated SPR sensor slide under the following conditions: no ATP in the perfusion buffer, 1 mM ATP in the perfusion buffer, 1 mM ATP and 0.1 mM GA in the perfusion buffer, or 1 mM ATP and 0.1 mM NECA in the perfusion buffer; Hsp90 and GRP94 were used at 100 mg/ml concentrations; arrowheads denote the time point at which the ligand was removed from the perfusion buffer; one of several representative experiments is shown; in panel b, the *** indicates all experimental conditions other than GRP94+ATP.
Figure 18:
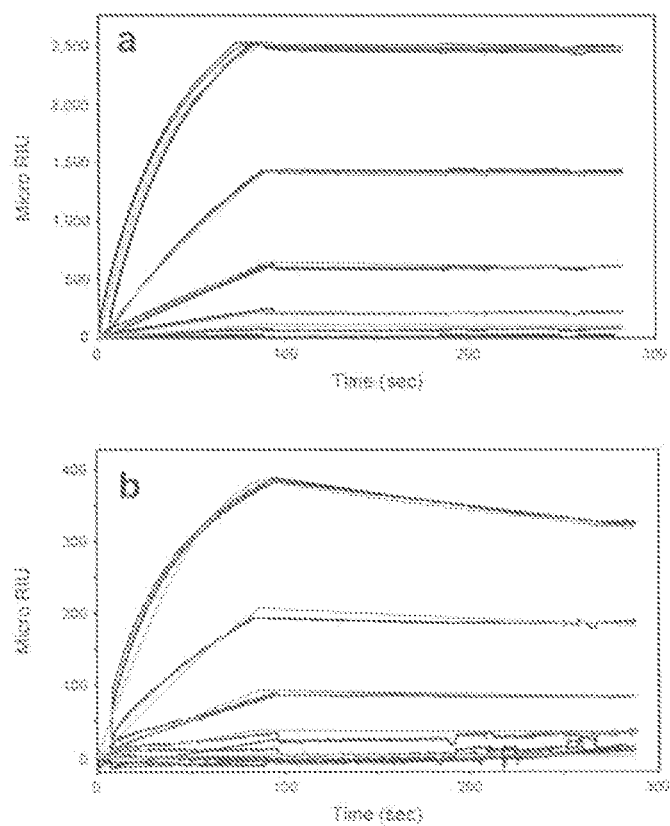
FIG. 18 shows binding of CTA1 to Hsp90 or GRP94; Hsp90 (a) or GRP94 (b) were perfused over a CTA1-coated SPR sensor slide at 100, 400, 800, 1,600, and 3,200 nM concentrations; (b): GRP94 was perfused over a CTA1-coated SPR sensor slide at concentrations of 100, 400, 800, and 1,600 nM; note that the results for Hsp90 and GRP94 are plotted on different scales; for all conditions, 1 mM ATP was present in the perfusion buffer; measurements were performed in three independent experiments with three different CTA1 sensor slides; all the collected data are shown; the red lines represent best fit curves derived from the raw data using 1:2 (CTA1:Hsp90 or CTA1:GRP94) binding models; the SPR traces display, from the top to the bottom of the graph, results for decreasing concentrations of the ligand.

Hsp90 functions in toxin translocation across the endosomal membrane, but its potential role in ERAD-mediated toxin dislocation has not been examined. To address this issue, surface plasmon resonance (SPR) was used to determine whether Hsp90 could directly interact with the isolated CTA1 subunit. Hsp90 binding to CTA1 occurred in an ATP-dependent manner that was blocked by GA (FIG. 17A). The interaction between CTA1 and Hsp90-ATP was not affected by NECA, a drug that inhibits GRP94 but not Hsp90 (FIG. 17A). GRP94, an ER-localized Hsp90, also bound to CTA1 in an ATP-dependent process that was blocked by both GA and NECA (FIG. 17B). The interaction between Hsp90 and CTA1 was much stronger than the interaction between GRP94 and CTA1: Hsp90 bound to CTA1 with a KD of 7 nM, whereas GRP94 bound to CTA1 with a KD of 292 nM (FIG. 18 and Table 2). The specific, high-affinity interaction between Hsp90-ATP and CTA1 indicated that Hsp90 could be involved with the CT intoxication process.

Figure 19:
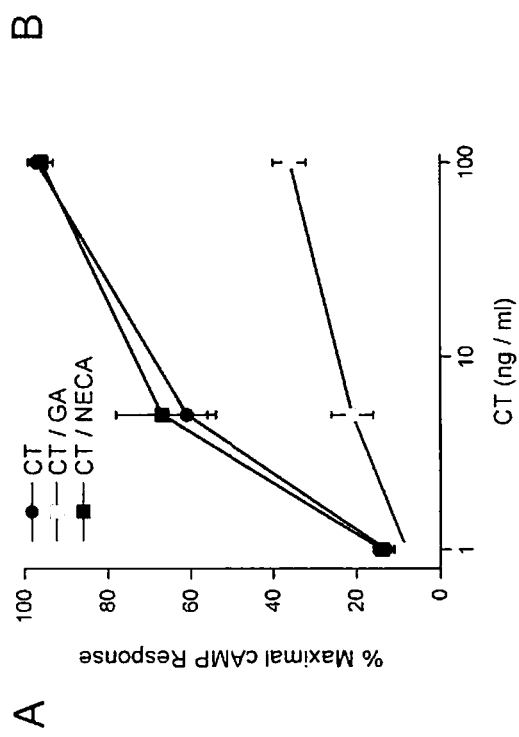
FIG. 19 GA but not NECA inhibits CT intoxication; (a): CHO cells were incubated with varying concentrations of CT in the absence of additional treatment, in the presence of 0.1 mM GA, or in the presence of 0.1 mM NECA; after two hours of continual toxin exposure, toxicity was assessed from the elevated levels of intracellular cAMP; the averages±standard errors of the means of at least four independent experiments with triplicate samples are shown; (b): CHO cells were incubated for 4 hours with varying concentrations of ricin in the absence or presence of 0.1 mM NECA; toxicity was then determined from the incorporation of [$^{35}$S]methionine into newly synthesized proteins; the averages±ranges of two independent experiments with triplicate samples are shown; (c): mock/CT/CT+GA/GA/forskolin/forskolin+GA.

To detect a functional role for Hsp90 in CT intoxication, CT toxicity assays were performed in the presence or absence of GA (FIG. 19A). CT activates Gsa, which in turn stimulates the activity of adenylate cyclase and the production of cAMP. CHO cells treated with GA exhibited substantial resistance to CT. In contrast, NECA-treated cells produced the same response to CT as the untreated cells. GA-induced toxin resistance was therefore due to the inactivation of Hsp90 rather than to the inactivation of GRP94. NECA-treated cells were resistant to ricin, another AB toxin that uses the ERAD system for A chain dislocation to the cytosol (FIG. 19B). This observation was consistent with published results and demonstrated that NECA was functional at the concentration used in our CT assay. Inactivation of Hsp90 thus provided cellular protection against CT. Additional control experiments demonstrated that GA did not inhibit the forskolin-induced elevation of intracellular cAMP: cells treated with GA and forskolin produced 100±2% of the cAMP levels recorded for cells treated with forskolin alone (n=3). Forskolin activates adenylate cyclase without the input of Gsa, so this observation demonstrated that GA did not directly inhibit the production of cAMP by adenylate cyclase.

GA also inhibited CT activity in the ileal loop model of intoxication (FIG. 19C). Surgically sealed sections of intestine were injected with 1 mg of CT in the absence or presence of GA. Following a time interval, the CT-injected loop displayed the distended morphology indicative of water accumulation resulting from productive intoxication. In contrast, substantially less fluid accumulation was observed in the loop that was injected with both CT and 1 mM GA. GA derivatives have also been evaluated as anti-cancer agents in phase I clinical trials. The protective effect of GA in a physiological model of intoxication suggests that it could also be used as a therapeutic to prevent or treat cholera.

Figure 20:
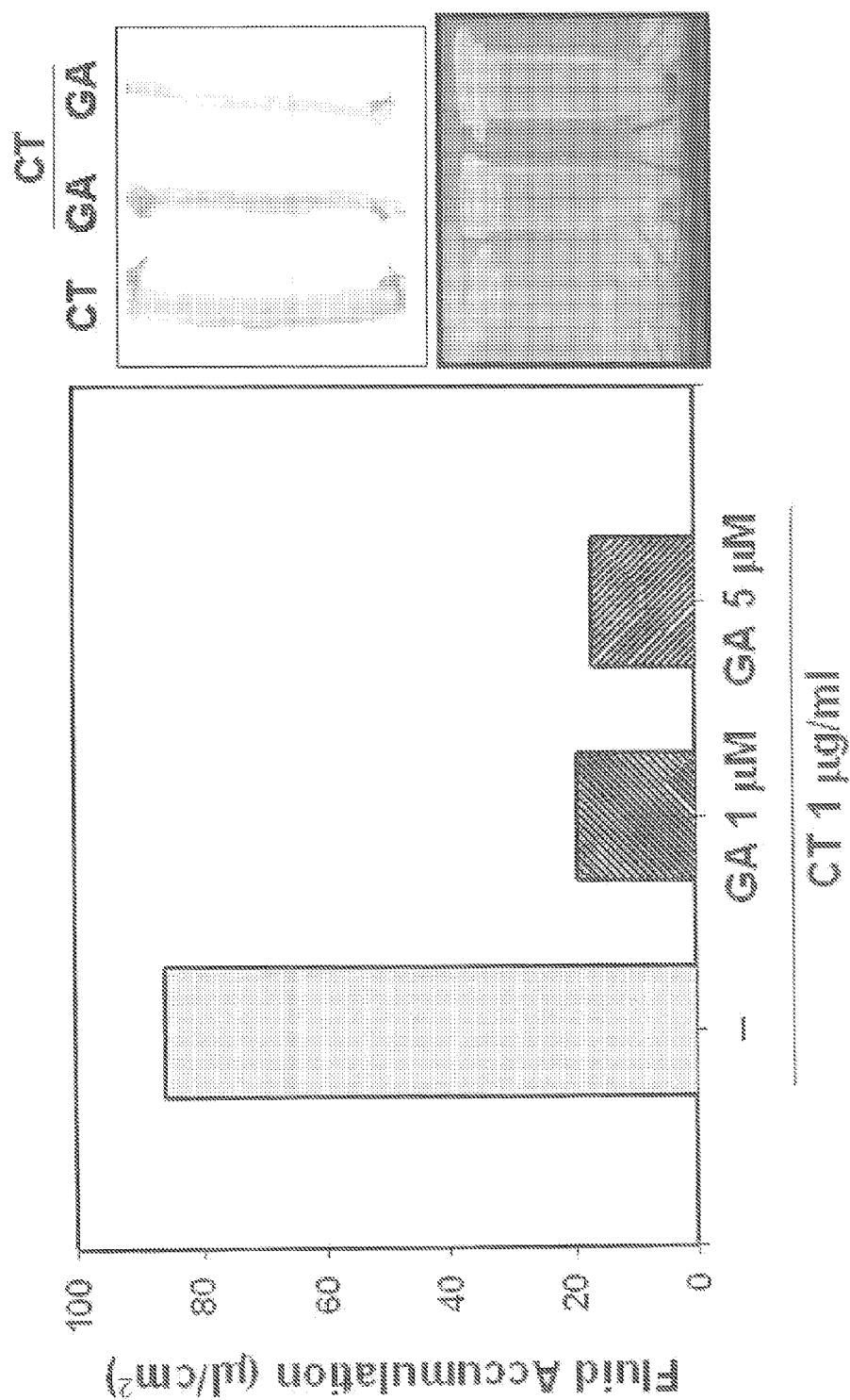
FIG. 20 shows that GA also inhibited CT activity in the ileal loop model of intoxication; surgically sealed sections of intestine were injected with 1 mg of CT in the absence or presence of GA; hours later, the CT-injected loop displayed the distended morphology indicative of water accumulation resulting from productive intoxication; in contrast, loops that were injected with both CT and 1 or 5 uM GA exhibited a minimal amount of fluid accumulation and intestinal distension; while GA derivatives have been evaluated by others as anti-cancer agents in phase I clinical trials, the protective effect of GA in a physiological model of intoxication is strongly suggestive that it could also be used as a therapeutic to prevent or treat cholera.
Figure 21:
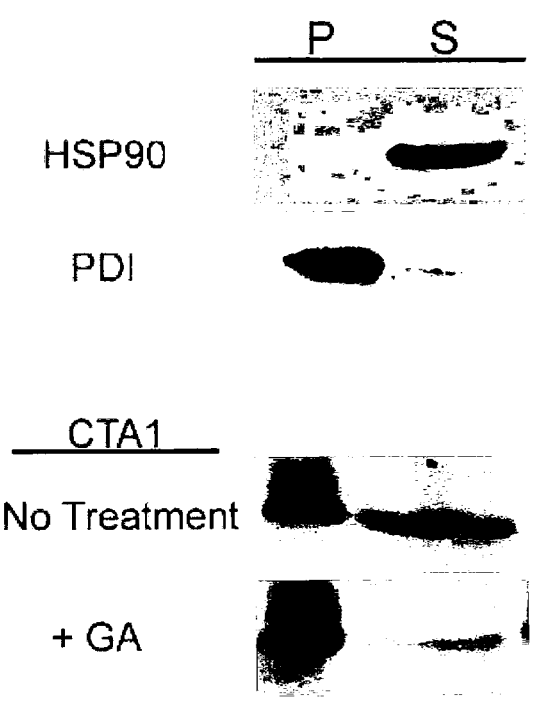
FIG. 21 shows that 4-phenylbutyric acid (PBA) and geldanamycin (GA) prevent the catalytic subunit of cholera toxin (CTA1) from entering the cytosol of target cells; HeLa cells were pulse-labeled at 4° C. for 30 min with 1 mg/ml of CT; the cells were then chased for 2 hr at 37° C. in toxin-free medium or toxin-free medium that contained either PBA, GA, NECA, or brefeldin A (BfA); selective permeabilization of the plasma membrane with digitonin was used to partition cell extracts into separate membrane and cytosolic fractions; a surface plasmon resonance (SPR) sensor slide coated with an anti-CTA antibody was used to detect the cytosolic pools of CTA1; CTA standards (1 ng/ml and 0.1 ng/ml) were perfused over the sensor slide as positive controls, and the cytosolic extract from unintoxicated cells was perfused over the slide as a negative control; an increase in the SPR response signal indicates ligand binding to the plate; these data demonstrate that less CTA1 was found in the cytosol of PBA- or GA-treated cells than in the cytosol of cells chased in the absence of drug treatment; NECA, a drug that inhibits GRP94 but not Hsp90, did not inihbit the appearance of CTA1 in the cytosol; BfA is a (toxic) drug known to inhibit toxin trafficking to the ER, and, thus, toxin passage into the cytosol; at the end of each experiment, bound sample was stripped from the sensor slide with a PBST wash at pH 6.0.
Figure 21:
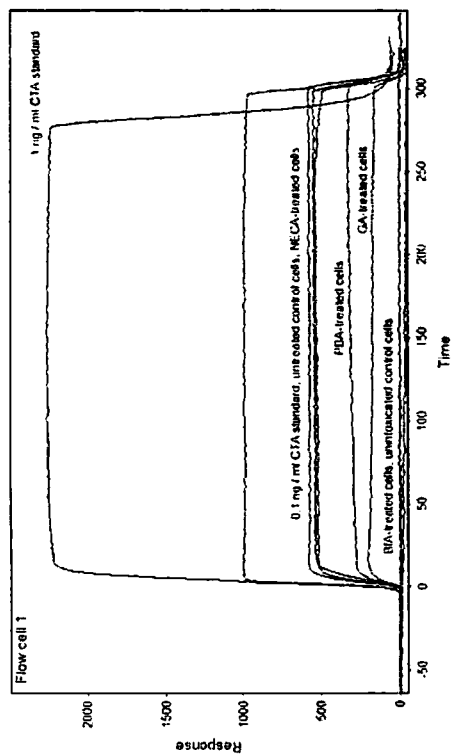
Figure 22:
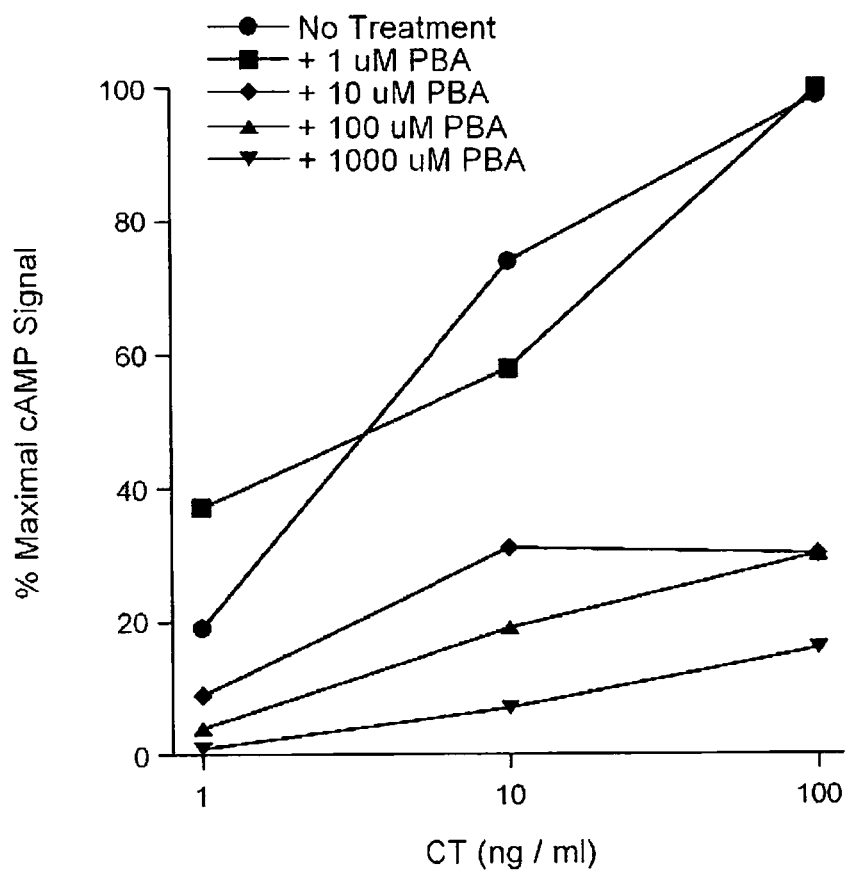
FIG. 22 shows how 4-phenylbutyric acid (PBA) inhibits cholera intoxication in a dose-dependent manner; CHO cells were incubated with varying concentrations of cholera toxin (CT) in the absence of additional treatment or in the presence of the indicated PBA concentrations; after 2 hours of continual toxin exposure, toxicity was assessed from the elevated levels of cAMP.
Figure 23:
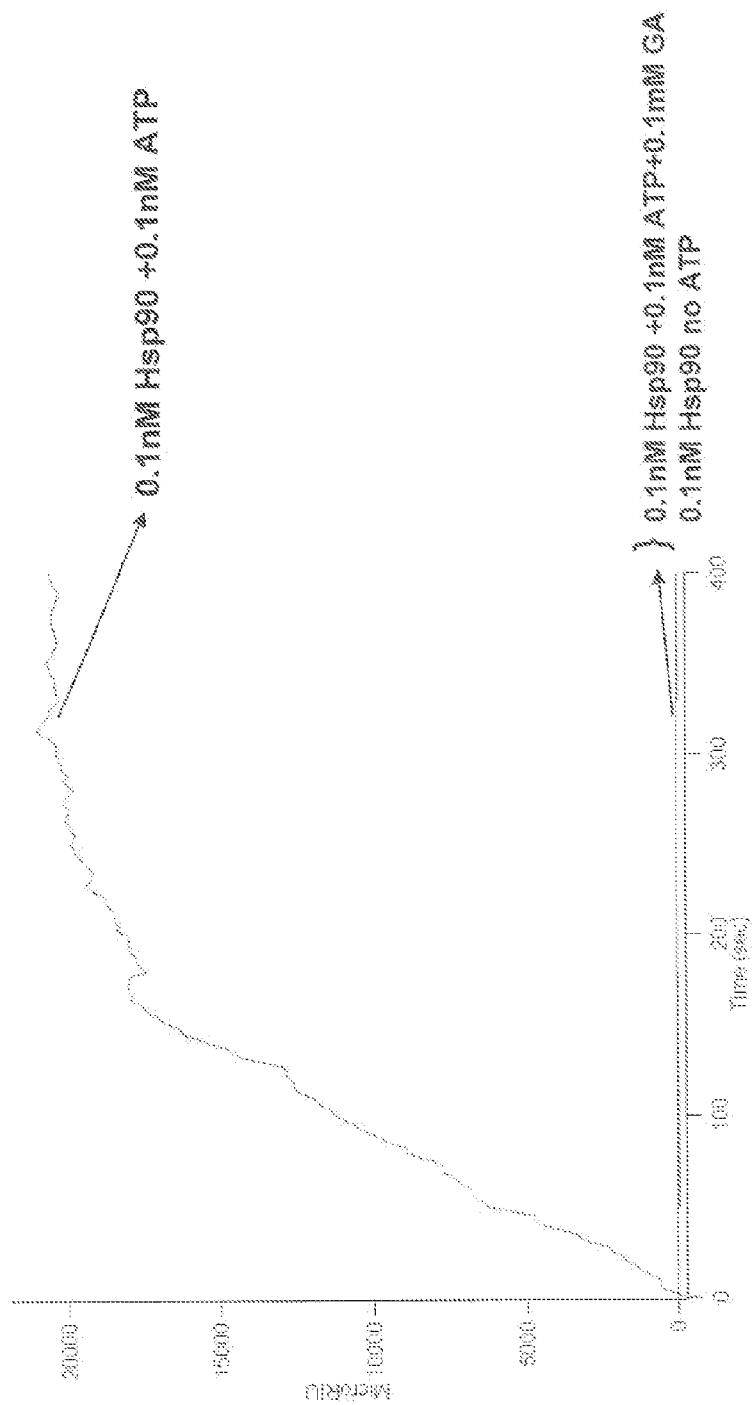
FIG. 23 presents data showing the Hsp90 inhibitor geldanamycin (GA) blocks the interaction between Hsp90 and the catalytic A subunit of pertussis toxin (PTS1); surface plasmon resonance (SPR) was used to characterize the interaction between Hsp90 and PTS1; an increase in the Micro Refractive Index Units (Micro RIU) is indicative of a physical interaction between two proteins; Hsp90 was perfused over an PTS1-coated SPR sensor slide under the following conditions: no ATP in the buffer, ATP in the buffer, or both GA and ATP in the buffer; the binding of Hsp90 to client proteins is an ATP-dependent process; the lack of interaction between Hsp90 and PTS1 in the absence of ATP or in the presence of GA demonstrates the specificity of the protein-protein interaction.
Figure 24:
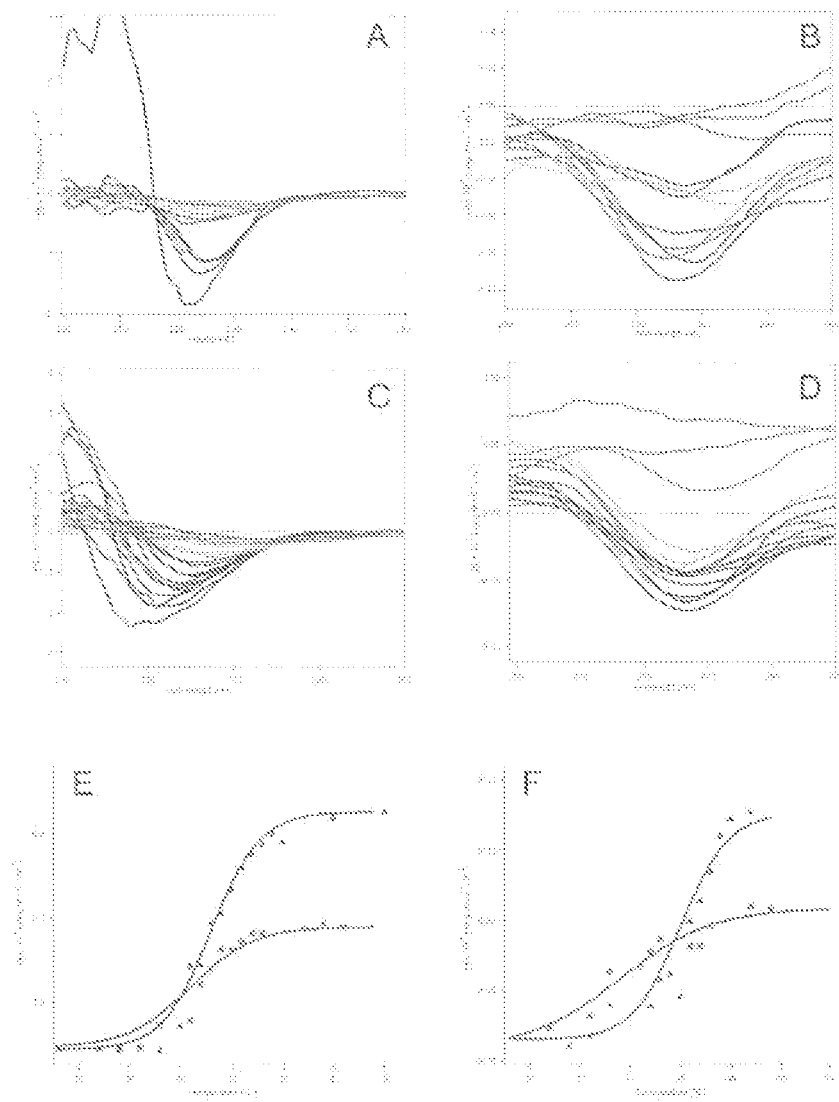
FIG. 24 shows the thermal stabilization of the catalytic subunit of pertussis toxin (PTS1) by 4-phenylbutyric acid (PBA); (A-D): the temperature-induced unfolding of PTS1 in the absence (A-B) or presence (C-D) of 0.1 mM PBA was monitored by far-UV CD (A, C) and near-UV CD (B, D); the change in color from blue to red corresponds to a change in temperature from 18° C. to 65° C.; (E-F): thermal unfolding profiles for PTS1 in the absence (red) or presence (blue) of PBA were derived from the data presented in panels A-D; (E): for far-UV CD analysis, the mean residue molar ellipticities at 220 nm ([θ]220) were plotted as a function of temperature; (F): for near-UV CD analysis, the mean residue molar ellipticities at 280 nm ([θ]280) were plotted as a function of temperature.
Figure 25:
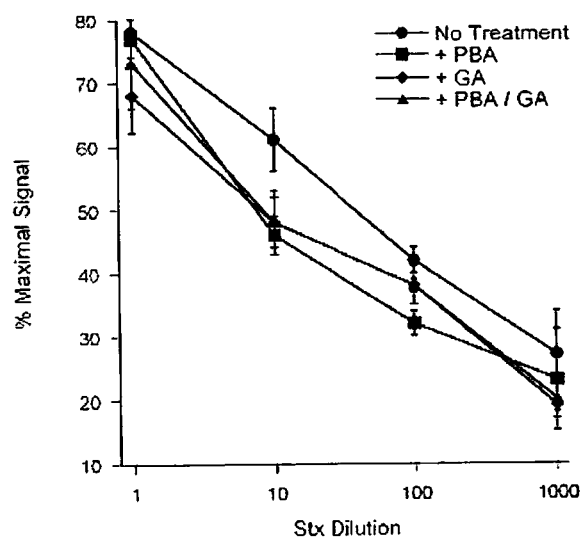
FIG. 25 resents data indicating that geldanamycin (GA) and 4-phenylbutyric acid (PBA) do not protect cultured cells against Shiga toxin; Vero cells expressing a destabilized variant of green fluorescent protein (t1/2=2 hr) were exposed to Ham's F-12 medium containing tenfold dilutions of culture supernatants from Shiga toxin-producing *E. coli* O157 strain RM1697; cells were challenged with toxin in the absence of additional treatment, in the presence of 0.1 mM GA, in the presence of 100 mM PBA, or in the presence of both 0.1 mM GA and 100 mM PBA; after 16 hr of intoxication, fluorescent output was recorded with a plate reader; Shiga toxin inhibits protein synthesis, so intoxicated cells will degrade the destabilized green fluorescent protein and will not produce more of the protein, which thus generates a decrease in the fluorescent signal; the fluorescent output from cells not exposed to toxin was used to establish the maximal signal, and all other results were expressed as a percentage of this signal; the averages±standard errors of the means of four independent experiments with six replicate samples for each condition are shown.

Toxin resistance can result from an inhibition of toxin dislocation from the ER to the cytosol. To determine if GA blocked toxin export to the cytosol, we used an established dislocation assay to monitor the appearance of CTA1 in the cytosol of intoxicated HeLa cells (FIG. 4). Like CHO cells, GA-treated HeLa cells were protected from CT (data not shown). After a 30 minute exposure to CT at 4° C., HeLa cells were chased for two hours at 37° C. in the absence of additional toxin. Separate organelle and cytosol fractions were then collected from digitonin permeabilized cells. Control experiments demonstrated the fidelity of our fractionation protocol: Western blot analysis detected the majority of Hsp90 in the supernatant (i.e., cytosolic) fraction, while protein disulfide isomerase (PDI), a soluble ER protein, was found exclusively in the pellet fraction which contained the intact ER and other membranes (FIG. 20A). The distributions of Hsp90 and PDI were unaffected by treatment with GA or NECA. In comparison to the untreated control cells, the distribution of CTA1 in the cytosol of intoxicated cells was also unaffected by NECA treatment. However, GA-treated cells contained less cytosolic CTA1 than either untreated or NECA-treated cells. It thus appeared that Hsp90 function was required for efficient passage of CTA1 into the cytosol.

To strengthen our Western blot analysis with a more sensitive detection method, we employed the technique of SPR. HeLa cells exposed to CT at 4° C. were again fractionated into membrane and cytosolic components after a 2 hour chase at 37° C. In this experiment, the cytosolic fractions were perfused over a SPR sensor slide that had been coated with an anti-CTA antibody (FIG. 20B). A negligible background signal was obtained from unintoxicated cells, whereas cells intoxicated in the absence of drug treatment produced a response that was equivalent the signal from the 0.1 ng/ml CTA standard. Cells intoxicated in the presence of NECA produced a response comparable to the response from cells intoxicated in the absence of drug treatment. In contrast, cells intoxicated in the presence of GA produced a weak SPR signal that was much less than the signal obtained from the 0.1 ng/ml CTA standard.

Recently, Hsp90 was shown to be involved with the renaturation of an unfolded protein that had passed from the cell surface to the ER and from the ER to the cytosol. The Hsp90-assisted refolding of denatured proteins may be linked to its dislocation activity: by coupling dislocation with refolding, Hsp90 would prevent the (re)folded CTA1 protein from sliding back into the dislocation pore. This ratchet mechanism would thus provide the driving force for CTA1 dislocation. Although a previous report had suggested that the ATP-dependent dislocation of CTA1 does not require cytosolic factors, we and others have detected a membrane-associated pool of Hsp90 which may have been purified with the microsomal preparation used in that study. Our work clearly shows that Hsp90 exhibits a high affinity interaction with CTA1, and that the GA-induced disruption of this interaction inhibits both CTA1 dislocation and CT intoxication in vivo.

Hsp90 is also involved with ricin intoxication, although in this case Hsp90 apparently prepares the catalytic toxin A chain for proteasomal degradation. The GA-induced inactivation of Hsp90 thus allows ricin A chain to accumulate in the cytosol and thereby generates cellular sensitization to ricin. In contrast, we have shown that GA-treated cells are resistant to CT. The dislocation of ricin A chain also involves GRP94 and p97 whereas these proteins do not appear to be active in CTA1 dislocation. Thus, while both CTA1 and ricin A chain exploit ERAD for passage into the cytosol, distinct molecular events are involved with the dislocation of the two toxins.

Hsp90 has been shown to maintain membrane-embedded ERAD substrates in a soluble state and to help determine the fate of misfolded proteins. This work establishes a new role for Hsp90 in the extraction of a soluble ERAD substrate from the ER. Methods, toxicity assays and dislocation assays performed in this section of our investigation are as described above.

TABLE 2

CTA1 exhibits a high affinity interaction with Hsp90 and a lower affinity interaction with GRP94.

| CTA1 binding partner | ka (1/Ms) | kd (1/s) | KD (nM) |
|---|---|---|---|
| Hsp90 | 9,929 | $7.8 \times 10^{-5}$ | 7 |
| Grp94 | 1,537 | $4.5 \times 10^{-4}$ | 292 |

On rates (ka), off rates (kd), and equilibrium dissociation constants (KD) between CTA1 and either Hsp90 or GRP94 were calculated from the data presented in FIG. 8.

TABLE 3

| Pertussis toxin | | |
|---|---|---|
| Conc (PBA in μM) | Near UV (° C.) | Far UV (° C.) |
| 0 | 29.0 | 31.0 |
| 100 | 36.0 | 33.0 |

The transition temperature (midpoint of transition from folded to unfolded conformations) for PTS1 in the absence or presence of PBA was calculated from far- and near-UV CD data. Near-UV CD monitors changes in tertiary structure; far-UV CD monitors changes in secondary structure. Higher transition temperatures reflect increased protein stability.

Accordingly, in the drawings and specification there have been disclosed typical preferred embodiments of the invention and although specific terms may have been employed, the terms are used in a descriptive sense only and not for purposes of limitation. The invention has been described in considerable detail with specific reference to these illustrated embodiments. It will be apparent, however, that various modifications and changes can be made within the spirit and scope of the invention as described in the foregoing specification and as defined in the appended claims.

LITERATURE CITED

1. De Haan, L. & Hirst, T. R. (2004). Cholera toxin: a paradigm for multi-functional engagement of cellular mechanisms. Mol Membr Biol 21, 77-92.
2. Sanchez, J. & Holmgren, J. (2008). Cholera toxin structure, gene regulation and pathophysiological and immunological aspects. Cell Mol Life Sci 65, 1347-1360.
3. Fishman, P. H. (1982). Internalization and degradation of cholera toxin by cultured cells: relationship to toxin action. J Cell Biol 93, 860-865.
4. Tran, D., Carpentier, J. L., Sawano, F., Gorden, P. & Orci, L. (1987). Ligands internalized through coated or non-coated invaginations follow a common intracellular pathway. Proc Natl Acad Sci USA 84, 7957-7961.
5. Orlandi, P. A., Curran, P. K. & Fishman, P. H. (1993). Brefeldin A blocks the response of cultured cells to cholera toxin. Implications for intracellular trafficking in toxin action. J Biol Chem 268, 12010-12016.
6. Lencer, W. I. & Tsai, B. (2003). The intracellular voyage of cholera toxin: going retro. Trends Biochem Sci 28, 639-645.
7. Orlandi, P. A. (1997). Protein-disulfide isomerase-mediated reduction of the A subunit of cholera toxin in a human intestinal cell line. J Biol Chem 272, 4591-4599.
8. Majoul, I., Ferrari, D. & Soling, H. D. (1997). Reduction of protein disulfide bonds in an oxidizing environment. The disulfide bridge of cholera toxin A-subunit is reduced in the endoplasmic reticulum. FEBS Lett 401, 104-108.
9. Tsai, B., Rodighiero, C., Lencer, W. I. & Rapoport, T. A. (2001). Protein disulfide isomerase acts as a redox-dependent chaperone to unfold cholera toxin. Cell 104, 937-948.
10. Teter, K., Allyn, R. L., Jobling, M. G. & Holmes, R. K. (2002). Transfer of the cholera toxin A1 polypeptide from the endoplasmic reticulum to the cytosol is a rapid process facilitated by the endoplasmic reticulum-associated degradation pathway. Infect Immun 70, 6166-6171.
11. Teter, K. & Holmes, R. K. (2002). Inhibition of endoplasmic reticulum-associated degradation in CHO cells resistant to cholera toxin, Pseudomonas aeruginosa exotoxin A, and ricin. Infect Immun 70, 6172-6179.
12. Teter, K., Jobling, M. G. & Holmes, R. K. (2003). A class of mutant CHO cells resistant to cholera toxin rapidly degrades the catalytic polypeptide of cholera toxin and exhibits increased endoplasmic reticulum-associated degradation. Traffic 4, 232-242.
13. Winkeler, A., Godderz, D., Herzog, V. & Schmitz, A. (2003). BiP-dependent export of cholera toxin from endoplasmic reticulum-derived microsomes. FEBS Lett 554, 439-442.
14. Vembar, S. S. & Brodsky, J. L. (2008). One step at a time: endoplasmic reticulum-associated degradation. Nat Rev Mol Cell Biol 9, 944-957.
15. Schmitz, A., Herrgen, H., Winkeler, A. & Herzog, V. (2000). Cholera toxin is exported from microsomes by the Sec61p complex. J Cell Biol 148, 1203-1212.
16. Bernardi, K. M., Forster, M. L., Lencer, W. I. & Tsai, B. (2008). Derlin-1 facilitates the retro-translocation of cholera toxin. Mol Biol Cell 19, 877-884.
17. Dixit, G., Mikoryak, C., Hayslett, T., Bhat, A. & Draper, R. K. (2008). Cholera toxin up-regulates endoplasmic reticulum proteins that correlate with sensitivity to the toxin. Exp Biol Med (Maywood) 233, 163-175.
18. Rodighiero, C., Tsai, B., Rapoport, T. A. & Lencer, W. I. (2002). Role of ubiquitination in retro-translocation of cholera toxin and escape of cytosolic degradation. EMBO Rep 3, 1222-1227.
19. Sandvig, K. & van Deurs, B. (2002). Membrane traffic exploited by protein toxins. Annu Rev Cell Dev Biol 18, 1-24.
20. Lord, J. M., Roberts, L. M. & Lencer, W. I. (2005). Entry of protein toxins into mammalian cells by crossing the endoplasmic reticulum membrane: co-opting basic mechanisms of endoplasmic reticulum-associated degradation. Curr Top Microbiol Immunol 300, 149-168.
21. Hazes, B. & Read, R. J. (1997). Accumulating evidence suggests that several AB-toxins subvert the endoplasmic reticulum-associated protein degradation pathway to enter target cells. Biochemistry 36, 11051-11054.
22. Teter, K., Jobling, M. G., Sentz, D. & Holmes, R. K. (2006). The cholera toxin A13 subdomain is essential for interaction with ADP-ribosylation factor 6 and full toxic activity but is not required for translocation from the endoplasmic reticulum to the cytosol. Infect Immun 74, 2259-2267.
23. Ampapathi, R. S., Creath, A. L., Lou, D. I., Craft, J. W., Jr., Blanke, S. R. & Legge, G. B. (2008). Order-disorder-order transitions mediate the activation of cholera toxin. J Mol Biol 377, 748-760.
24. Pande, A. H., Scaglione, P., Taylor, M., Nemec, K. N., Tuthill, S., Moe, D., Holmes, R. K., Tatulian, S. A. & Teter, K. (2007). Conformational instability of the cholera toxin A1 polypeptide. J Mol Biol 374, 1114-1128.
25. Goins, B. & Freire, E. (1988). Thermal stability and intersubunit interactions of cholera toxin in solution and in association with its cell-surface receptor ganglioside GM1. Biochemistry 27, 2046-2052.
26. Surewicz, W. K., Leddy, J. J. & Mantsch, H. H. (1990). Structure, stability, and receptor interaction of cholera toxin as studied by Fourier-transform infrared spectroscopy. Biochemistry 29, 8106-8111.
27. Murayama, T., Tsai, S.C., Adamik, R., Moss, J. & Vaughan, M. (1993). Effects of temperature on ADP-ribosylation factor stimulation of cholera toxin activity. Biochemistry 32, 561-566.
28. Forster, M. L., Sivick, K., Park, Y. N., Aryan, P., Lencer, W. I. & Tsai, B. (2006). Protein disulfide isomerase-like proteins play opposing roles during retrotranslocation. J Cell Biol 173, 853-859.
29. Coux, O., Tanaka, K. & Goldberg, A. L. (1996). Structure and functions of the 20S and 26S proteasomes. Annu Rev Biochem 65, 801-847.
30. Romisch, K. (2004). A cure for traffic jams: small molecule chaperones in the endoplasmic reticulum. Traffic 5, 815-820.
31. Shearer, A. G. & Hampton, R. Y. (2004). Structural control of endoplasmic reticulum-associated degradation:

effect of chemical chaperones on 3-hydroxy-3-methylglutaryl-CoA reductase. J Biol Chem 279, 188-196.
32. Sato, S., Ward, C. L., Krouse, M. E., Wine, J. J. & Kopito, R. R. (1996). Glycerol reverses the misfolding phenotype of the most common cystic fibrosis mutation. J Biol Chem 271, 635-638.
33. Burrows, J. A., Willis, L. K. & Perlmutter, D. H. (2000). Chemical chaperones mediate increased secretion of mutant alpha 1-antitrypsin (alpha 1-AT) Z: A potential pharmacological strategy for prevention of liver injury and emphysema in alpha 1-AT deficiency. Proc Natl Acad Sci USA 97, 1796-1801.
34. Brown, C. R., Hong-Brown, L. Q., Biwersi, J., Verkman, A. S. & Welch, W. J. (1996). Chemical chaperones correct the mutant phenotype of the delta F508 cystic fibrosis transmembrane conductance regulator protein. Cell Stress Chaperones 1, 117-125.
35. Sandvig, K., Madshus, I. H. & Olsnes, S. (1984). Dimethyl sulphoxide protects cells against polypeptide toxins and poliovirus. Biochem J 219, 935-940.
36. Quinones, B., Massey, S., Friedman, M., Swimley, M. S. & Teter, K. (2009). Novel cell-based method to detect Shiga toxin 2 from *Escherichia coli* O157:H7 and inhibitors of toxin activity. Appl Environ Microbiol 75, 1410-1416.
37. Argent, R. H., Parrott, A. M., Day, P. J., Roberts, L. M., Stockley, P. G., Lord, J. M. & Radford, S. E. (2000). Ribosome-mediated folding of partially unfolded ricin A-chain. J Biol Chem 275, 9263-9269.
38. Swaisgood, H. E. (1993). Review and update of casein chemistry. J Dairy Sci 76, 3054-3061.
39. Lencer, W. I., de Almeida, J. B., Moe, S., Stow, J. L., Ausiello, D. A. & Madara, J. L. (1993). Entry of cholera toxin into polarized human intestinal epithelial cells. Identification of an early brefeldin A sensitive event required for A1-peptide generation. J Clin Invest 92, 2941-2951.
40. Guerra, L., Teter, K., Lilley, B. N., Stenerlow, B., Holmes, R. K., Ploegh, H. L., Sandvig, K., Thelestam, M. & Frisan, T. (2005). Cellular internalization of cytolethal distending toxin: a new end to a known pathway. Cell Microbiol 7, 921-934.
41. Sacksteder, C. A., Whittier, J. E., Xiong, Y., Li, J., Galeva, N. A., Jacoby, M. E., Purvine, S. O., Williams, T. D., Rechsteiner, M. C., Bigelow, D. J. & Squier, T. C. (2006). Tertiary structural rearrangements upon oxidation of Methionine-145 in calmodulin promotes targeted proteasomal degradation. Biophys J 91, 1480-1493.
42. Aridor, M. (2007). Visiting the ER: the endoplasmic reticulum as a target for therapeutics in traffic related diseases. Adv Drug Deliv Rev 59, 759-781.
43. Pande, A. H., Moe, D., Jamnadas, M., Tatulian, S. A. & Teter, K. (2006). The pertussis toxin S1 subunit is a thermally unstable protein susceptible to degradation by the 20S proteasome. Biochemistry 45, 13734-13740.
44. Mayerhofer, P. U., Cook, J. P., Wahlman, J., Pinheiro, T. T., Moore, K. A., Lord, J. M., Johnson, A. E. & Roberts, L. M. (2009). Ricin A chain insertion into endoplasmic reticulum membranes is triggered by a temperature increase to 37° C. J Biol Chem 284, 10232-10242.
45. Homola, J. (2003). Present and future of surface plasmon resonance biosensors. Anal Bioanal Chem 377, 528-539.
46. Bech, E., Jakobsen, J. & Orntoft, T. F. (1994). ELISA-type titertray assay of IgM anti-GM1 autoantibodies. Clin Chem 40, 1331-1334.

The invention claimed is:

1. A method of inhibiting toxicity of a bacterial AB-type toxin for a susceptible host, the method comprising contacting the toxin with a compound which interferes with unfolding of the toxin at the host's physiologic temperature, wherein the toxin comprises cholera toxin or *E. coli* heat labile toxin and wherein the compound is sodium 4-phenylbutyrate.

2. The method of claim 1, wherein the compound comprises sodium-4-phenylbutyrate (PBA) orally administered to the host.

3. The method of claim 1, wherein the compound comprises sodium 4-phenylbutyrate (PBA) dissolved in the host's fluids.

4. The method of claim 1, wherein the susceptible host comprises mammalian cells.

5. The method of claim 1, wherein the susceptible host comprises a human.

6. A method of inhibiting toxicity of a bacterial AB-type ADP-ribosylating toxin for a susceptible host, the method comprising contacting the toxin with a compound which interferes with unfolding of the toxin in host cells or with release of the toxin into host cells' cytosol, wherein the toxin comprises cholera toxin and wherein the compound is sodium 4-phenylbutyrate.

7. The method of claim 6, wherein the compound comprises sodium-4-phenylbutyrate (PBA) orally administered to the susceptible host.

8. The method of claim 6, wherein the compound comprises sodium 4-phenylbutyrate (PBA) dissolved in the susceptible host's fluids.

9. The method of claim 6, wherein the susceptible host comprises mammalian cells.

10. The method of claim 6, wherein the susceptible host comprises human cells.

11. The method of claim 6, wherein the susceptible host is a human.

12. A method of treating a mammalian cell intoxicated with a bacterial AB-type ADP-ribosylating toxin, the method comprising administering to the cell a compound which interferes with thermal unfolding of the toxin molecule in the cell, wherein the toxin comprises cholera toxin or *E. coli* heat labile toxin and wherein the compound is sodium 4-phenylbutyrate.

13. A method of treating a mammalian cell intoxicated with a bacterial AB-type ADP-ribosylating toxin, the method comprising administering to the cell a compound which interferes with endoplasmic reticulum export of the toxin into the cytosol, wherein the toxin comprises cholera toxin or *E. coli* heat labile toxin and wherein the compound is sodium 4-phenylbutyrate.

14. A method of treating a mammalian host intoxicated with a bacterial AB-type ADP-ribosylating toxin, the method comprising administering to the host a compound of sodium-4-phenylbutyrate (PBA), wherein the toxin comprises cholera toxin or *E. coli* heat labile toxin.

15. The method of claim 14, wherein the mammalian host comprises one or more mammalian cells.

16. The method of claim 14, wherein the mammalian host comprises a human host.

17. The method of claim 14, wherein administering further comprises orally administering sodium 4-phenylbutyrate.

* * * * *